United States Patent [19]

Heckendorn

[11] Patent Number: 4,510,141
[45] Date of Patent: Apr. 9, 1985

[54] TRICYCLIC POLYAZAHETEROCYCLES FOR TREATING DEPRESSION OR ANXIETY

[75] Inventor: Roland Heckendorn, Arlesheim, Switzerland

[73] Assignee: Ciba-Geigy Corporation, Ardsley, N.Y.

[21] Appl. No.: 417,788

[22] Filed: Sep. 13, 1982

[51] Int. Cl.³ .................. C07D 487/04; C07D 471/14; A61K 31/50; A61K 31/535
[52] U.S. Cl. .................................. 514/250; 260/243.3; 544/115; 544/346; 546/276; 548/262
[58] Field of Search ................ 544/346, 106; 426/250; 260/243.3; 424/248.52, 248.57, 248.4

[56] References Cited

U.S. PATENT DOCUMENTS 3,878,205 4/1975 Gagneux et al. ............... 424/267
4,235,775 11/1980 Meguro et al. ............. 260/239 BD

FOREIGN PATENT DOCUMENTS 0039920 9/1980 European Pat. Off. .

OTHER PUBLICATIONS

Yurugi et al., Chem. Abstracts, vol. 80, item 37073d, (1974).
Maki et al., Chem. Abstracts, vol. 81, item 152214h, (1974).
Hester et al., J. Med. Chem., vol. 23, pp. 392–402, (1980).

Primary Examiner—Mark L. Berch
Attorney, Agent, or Firm—Michael W. Glynn

[57] ABSTRACT

The invention relates to novel polycyclic polyazaheterocycles having psychopharmacological properties, especially antidepressive and anxiolytic activity, corresponding to the formula I

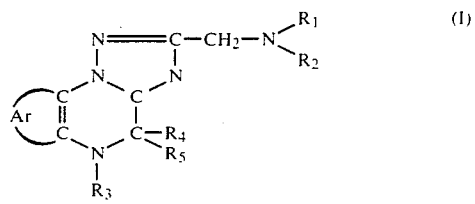

in which $R_1$ and $R_2$ each represents, independently of the other, hydrogen, lower alkyl or hydroxy-lower alkyl, or together represent lower alkylene or ethyleneoxyethylene, ethyleneazaethylene or N-lower alkyl- or N-(2-hydroxy-lower alkyl)-ethyleneazaethylene, $R_3$ represents hydrogen or a lower aliphatic hydrocarbon radical or a saturated lower cycloaliphatic hydrocarbon radical or unsubstituted or substituted phenyl, $R_4$ and $R_5$ represent hydrogen or lower alkyl, and Ar represents an unsubstituted or substituted benzo or pyrido radical, and to acid addition salts of compounds of the general formula I, especially the pharmaceutically acceptable acid addition salts of compounds of the general formula I, to pharmaceutical preparations containing these novel substances and to a method of treating conditions of depression or anxiety by administering them.

25 Claims, No Drawings

TRICYCLIC POLYAZAHETEROCYCLES FOR TREATING DEPRESSION OR ANXIETY

The invention relates to novel polycyclic polyazaheterocycles and their acid addition salts, to pharmaceutical preparations containing them and to the use of these novel substances and pharmaceutical compositions.

The novel compounds according to the invention correspond to the formula I

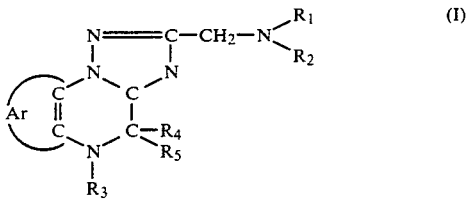

in which
R₁ and R₂ each represents, independently of the other, hydrogen, lower alkyl or hydroxy-lower alkyl, or together represent lower alkylene or ethyleneoxyethylene, ethyleneazaethylene or N-lower alkyl- or N-(2-hydroxy-lower alkyl)-ethyleneazaethylene,
R₃ represents hydrogen or a lower aliphatic hydrocarbon radical or a saturated lower cycloaliphatic hydrocarbon radical or unsubstituted or substituted phenyl,
R₄ and R₅ represent hydrogen or lower alkyl, and Ar represents an unsubstituted or substituted benzo or pyrido radical.

By a benzo or pyrido radical there is to be understood a divalent radical which together with the two adjacent carbon atoms forms a benzene or pyridine ring. The invention relates also to the acid addition salts of compounds of the general formula I, and especially to the pharmaceutically acceptable acid addition salts of compounds of the general formula I.

Unless otherwise stated, hereinbefore and hereinafter "lower" radicals are to be understood as those containing a maximum of 7, preferably a maximum of 4, carbon atoms. As a result of the close relationship between the compounds of the general formula I in the form of free bases and in the form of acid addition salts, hereinafter the bases or their acid addition salts shall be understood to mean optionally also the corresponding acid addition salts or free bases, respectively, wherever appropriate and meaningful.

Lower alkyl R₁ and/or R₂ is, for example, ethyl, propyl, isopropyl, butyl or isobutyl and, especially, methyl. In hydroxy-lower alkyl, R₁ and/or R₂ the hydroxy group is in a position higher than the 1-position; accordingly, such radicals are, for example, 2- or 3-hydroxypropyl, 2-, 3- or 4-hydroxybutyl and, especially, 2-hydroxyethyl. As lower alkylene, R₁ and R₂ together represent, for example, ethylene, trimethylene, hexamethylene and, especially, tetramethylene or pentamethylene, or correspondingly branched, that is to say lower alkylated, especially methylated, radicals, such as, for example, 1,4-dimethyltetramethylene or 3,3-dimethylpentamethylene. The lower alkyl in ethyleneazaethylene is, for example, ethyl, propyl, isopropyl and, especially, methyl, and 2-hydroxy-lower alkyl is, for example, 2-hydroxypropyl and, especially, 2-hydroxyethyl.

As a lower aliphatic hydrocarbon radical, R₃ is lower alkyl, lower alkenyl or lower alkynyl, each having a maximum of 7, preferably a maximum of 4, carbon atoms. As lower alkyl, R₃ is, for example, methyl, ethyl, propyl, isopropyl, butyl, isobutyl, sec.-butyl, pentyl, isopentyl, neopentyl, 1-methylbutyl, 1-ethylpropyl, hexyl, isohexyl, 1-methylpentyl, heptyl, isoheptyl, 1-methylhexyl or 1-propylbutyl; as lower alkenyl, R₃ is especially lower alkenyl having 3 or 4 carbon atoms, for example allyl, 1-methallyl, 2-methallyl, 2-butenyl or 3-butenyl, and as lower alkynyl, R₃ is, for example, 2-propynyl or 2-butynyl. As a saturated lower cycloaliphatic hydrocarbon radical, R₃ is especially cycloalkyl, lower alkylcycloalkyl or cycloalkyl-lower alkyl, each having a maximum of 7 carbon atoms, such as, for example, cyclopentyl, cyclohexyl, cycloheptyl or 2- or 4-methylcyclohexyl, or cyclopropylmethyl, cyclopentylmethyl, 2-cyclopentylethyl or cyclohexylmethyl.

Substituted phenyl R₃ is phenyl mono- or poly-substituted, for example, by halogen having an atomic number of up to 35, lower alkyl, lower alkoxy, lower alkylthio, trifluoromethyl, cyano and/or by nitro.

In a pyrido radical Ar the ring nitrogen atom may be in any of the four possible positions but is especially in the 4-position, and more especially in the 2-position, to the ring carbon atom that is bonded to the R₃-substituted nitrogen atom of the pyrazine ring. As a pyrido radical, Ar is thus, in relation to the central pyrazine ring, especially the pyrido[4,3-e] radical and more especially the pyrido[2,3-e] radical. Substituents of a benzo or pyrido radical Ar are, for example, halogen having an atomic number of up to 35, lower alkyl, lower alkoxy, lower alkylthio, trifluoromethyl, cyano or nitro.

As substituent of phenyl R₃ and/or as substituent of Ar, halogen is fluorine, bromine or, especially, chlorine; lower alkyl is, for example, ethyl, propyl, isopropyl, butyl or tert.-butyl and, especially, methyl; lower alkoxy is, for example, ethoxy, propoxy, isopropoxy, butoxy or isobutoxy and, especially, methoxy, and lower alkylthio is, for example, ethylthio, propylthio, isopropylthio, butylthio and, especially, methylthio. Lower alkyl R₄ is, for example, isopropyl or, preferably, primary lower alkyl, such as ethyl, propyl, isobutyl and, especially, methyl, and lower alkyl R₅ is preferably one of the above-mentioned primary lower alkyls, especially methyl together with methyl R₄.

As acid addition salts of compounds of the formula I there come into consideration especially pharmaceutically acceptable acid addition salts. These can be used optionally in the same manner as the free compounds of the general formula I as active ingredients for pharmaceutical preparations. Examples that may be mentioned are the addition salts with hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicylic acid, phenylacetic acid, mandelic acid and embonic acid.

The compounds of the general formula I and their acid addition salts exhibit valuable psychopharmacological properties. In particular they act antagonistically with respect to reserpine-induced hypothermia, for example in the case of intraperitoneal or peroral administration to rats [cf. Benz and Waser, *Arzneimittelforsch.* 21 (5) 654 (1971)] in a dosage range of from 10 to 100 mg/kg, and with respect to tetrabenazine-induced ptosis in the case of intraperitoneal or peroral administration to rats [cf. Rubin et al., *J. Pharmacol. exptl. Ther.* 120, 125 (1957)] in a dosage range of from 3 to 100 mg/kg. For example, the $ED_{50}$ of 2-[(dimethylamino)-methyl]-5-phenyl-4,5-dihydro-[1,2,4]triazolo[1,5-a]-quinoxaline hydrochloride in the second test mentioned is from 3 to 10 mg/kg per os and 10 mg/kg i.p.. In a social conflict test in rats, the compounds of the general formula I, such as the compound mentioned above, exhibit anxiolytic action after peroral administration of doses from 1 mg/kg. In contrast to the rather negatively inotropic and positively chronotropic action of some known antidepressives, such as imipramine, the compounds of the general formula I, such as the compound mentioned above, exhibit a weakly positively inotropic and weakly negatively chronotropic action on the isolated atrium of guinea pigs. The toxicity of the compounds of the general formula I is low in comparison with their desired pharmacological actions. These properties characterise the compounds of the general formula I as antidepressives and anxiolytics that can be used for the treatment of conditions of depression of anxiety in mammals.

The invention relates especially to compounds of the general formula I in which $R_1$ and $R_2$ have the meanings given under formula I, $R_3$ represents a lower aliphatic hydrocarbon radical or a saturated lower cycloaliphatic hydrocarbon radical or phenyl that is unsubstituted or substituted by halogen having an atomic number of up to 35, lower alkyl, lower alkoxy, lower alkylthio, trifluoromethyl, cyano or by nitro, and Ar represents a benzo or pyrido[2,3-e] radical that is unsubstituted or substituted by substituents of the above-mentioned types, and $R_4$ and $R_5$ have the meanings given under formula I, and acid addition salts, especially pharmaceutically acceptable acid addition salts, thereof.

The invention relates more especially to compounds of the general formula I in which $R_1$ represents lower alkyl and $R_2$ represents hydrogen or lower alkyl, or $R_1$ and $R_2$ together represent lower alkylene, $R_3$ represents phenyl that is unsubstituted or substituted by halogen having an atomic number of up to 35, or represents lower cycloalkyl, and Ar represents a benzo or pyrido[2,3-e] radical that is unsubstituted or substituted by halogen having an atomic number of up to 35, and $R_4$ and $R_5$ have the meanings given under formula I, and acid addition salts, especially pharmaceutically acceptable acid addition salts, thereof.

The invention relates very especially to compounds of the general formula I in which $R_1$ represents lower alkyl, especially methyl, and $R_2$ represents hydrogen or lower alkyl, especially methyl, or $R_1$ and $R_2$ together represent lower alkylene, especially tetramethylene, $R_3$ represents phenyl that is unsubstituted or substituted by halogen having an atomic number of up to 35, especially chlorine, and Ar represents a benzo radical that is unsubstituted or substituted by halogen having an atomic number of up to 35, especially chlorine, or represents the pyrido[2,3-e] radical, $R_4$ has the meaning given under formula I and $R_5$ represents hydrogen or methyl, and acid addition salts, especially pharmaceutically acceptable acid addition salts, thereof.

The invention relates most especially to compounds of the general formula I in which $R_1$ represents methyl, $R_2$ represents hydrogen or methyl, $R_3$ represents phenyl, $R_4$ represents hydrogen or methyl, $R_5$ represents methyl or, especially, hydrogen, and Ar represents the benzo or pyrido[2,3-e] radical, and acid addition salts, especially pharmaceutically acceptable acid addition salts, thereof.

The novel compounds are manufactured in a manner known per se, for example, by (a) reacting a reactive ester of a compound of the general formula II

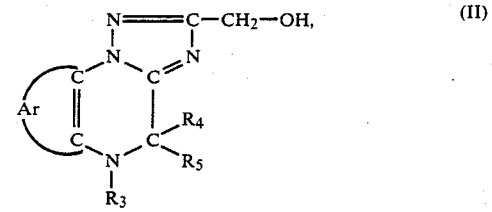

in which $R_3$, $R_4$, $R_5$ and Ar have the meanings given under formula I, with a compound of the general formula III

in which $R_1$ and $R_2$ have the meanings given under formula I, or (b) in a compound of the general formula IV

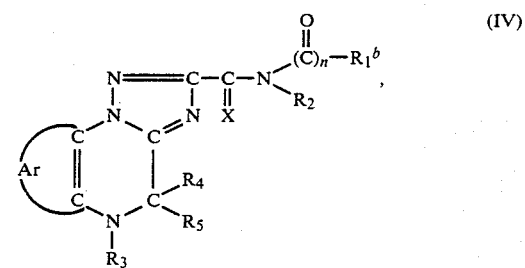

in which n represents 0 or 1 and X represents oxygen or, if n represents 1, can also represent two hydrogen atoms, $R_1^b$ alone and together with $R_2$ has the meaning of $R_1$ or, if n represents 1, can also represent lower alkoxy, and $R_2$, $R_3$, $R_4$, $R_5$ and Ar have the meanings given under formula I, reducing the carbonyl group(s) or the optionally present lower alkoxycarbonyl group by means of a hydride reducing agent, or (c) in a compound of the general formula I in which $R_3$ represents hydrogen and $R_1$, $R_2$, $R_4$, $R_5$ and Ar have the meanings given under formula I, introducing a radical $R_3$ that is other than hydrogen and that still has at least one hydrogen atom present at its bonding carbon atom, or (d) in a compound of the general formula I in which one or both of the symbols $R_1$ and $R_2$ represent(s) hydrogen and $R_3$, $R_4$, $R_5$ and Ar have the meanings given under formula I, introducing one or two radicals $R_1$ and/or $R_2$ that are other than hydrogen, and, if desired, converting a resulting compound of the general formula I into an acid addition salt with an inorganic or organic acid or freeing the base from a resulting acid addition salt and, if desired, converting it back into an acid addition salt.

For reactions according to (a) there are suitable as reactive esters of compounds of the general formula II, for example, esters of organic sulphonic acids, such as lower alkanesulphonic acid esters or arenesulphonic acid esters, for example methanesulphonic acid esters or benzenesulphonic acid or p-toluenesulphonic acid esters, or halides, especially bromides, chlorides or iodides. The reactions are carried out, for example, in an inert organic solvent at temperatures of from approximately 0° C. to approximately 100° C. or the boiling temperature of the solvent used if this is lower than 100° C., in the presence of an excess of the compound of the general formula III to be reacted or a tertiary organic base or an inorganic base, for example triethylamine, ethyldiisopropylamine or pyridine, or an alkali metal carbonate or bicarbonate, such as potassium carbonate or sodium bicarbonate, as acid-binding agent.

The reduction according to (b) of compounds of the general formula IV can be effected, for example, by means of a lower alkylaluminium hydride, such as diisobutylaluminium hydride, for example in an aromatic hydrocarbon, such as toluene, at temperatures of between approximately −10° C. and room temperature, or by means of lithium aluminium hydride or diborane in an ethereal solvent, such as diethyl ether or tetrahydrofuran, for example at temperatures of between room temperature and approximately 55° C. or the boiling temperature of the solvent if this is lower than 55° C.

The introduction of a radical $R_3$ that is other than hydrogen and still has at least one hydrogen atom present at its bonding carbon atom and is thus neither aromatic nor bonded via a quaternary carbon atom, into a compound of the general formula I according to (c) is effected especially by reaction of one of the latter compounds with a reactive ester of a secondary or, preferably, primary lower alkanol, lower alkenol or lower alkynol, or of a cycloalkanol having from 5 to 7 carbon atoms or of a preferably primary cycloalkyl-lower alkanol having from 4 to 7 carbon atoms. There are used as corresponding reactive esters, for example, hydrohalic acid esters, such as chlorides or, especially, bromides or iodides, or esters with organic sulphonic acids, such as lower alkanesulphonic acid or arenesulphonic acid esters, for example methanesulphonic acid esters or benzenesulphonic acid esters or p-toluenesulphonic acid esters, of methanol, ethanol, propanol, isopropanol, butanol, isobutanol, allyl alcohol, 2-methallyl alcohol, 2-propynol, cyclopentanol, cyclohexanol, cycloheptanol, cyclopropyl-, cyclobutyl-, cyclopentyl- or cyclohexylmethanol or 2-cyclopentylethanol. The reaction can be carried out in an inert organic solvent or diluent and, for example, at temperatures of between approximately 0° C. and 100° C., especially between room temperature and approximately 80° C. or the boiling temperature of the solvent if this is lower than 80° C., in the presence of a basic condensation agent, for example an alkali metal, alkali metal amide or hydride, or an alkali metal lower alkoxide, such as sodium or potassium methoxide, ethoxide or tert.-butoxide.

A primary radical $R_3$ can be introduced, for example, also by a two-step reaction sequence, by first acylating the compound of the general formula I in the 5-position to form the corresponding compound having the acyl radical of a lower alkanoic acid or cycloalkyl-lower alkanoic acid having a maximum of 7 carbon atoms and then reducing the latter compound analogously to process (b) by means of a hydride reducing agent.

The introduction of one or two radicals $R_1$ and/or $R_2$ that is or are other than hydrogen into a compound of the general formula I in which at least one of the symbols $R_1$ and $R_2$ represents hydrogen can be carried out, for example, by reaction of a corresponding compound of the general formula I with an equimolar amount or, if the case may be, at least double the molar amount of a reactive ester, for example a hydrohalic acid ester, such as a chloride or, especially, a bromide or iodide, or of an ester with an organic sulphonic acid, for example a lower alkanesulphonic acid or arenesulphonic acid ester, such as the methanesulphonic acid ester or the benzenesulphonic acid or p-toluenesulphonic acid ester of a non-tertiary lower alkanol or a corresponding mono- or di-ester of a lower alkanediol, for example a corresponding ester of methanol, ethanol, propanol, isopropanol or butanol, a corresponding monoester of 1,2-ethanediol or 1,2- or 1,3-propanediol or a corresponding mono- or di-ester of 1,4-butanediol or 1,5-pentanediol, substantially analogously to the reaction conditions given for process (a).

A further possibility for the introduction of radicals $R_1$ and/or $R_2$ that are other than hydrogen into compounds of the general formula I that are suitable for this purpose consists in reacting such compounds with oxo-lower alkanes, such as, for example, formaldehyde, acetaldehyde, acetone, 2-butanone or 3-pentanone, under reducing conditions, for example in the presence of formic acid at temperatures of from approximately 60° C. to approximately 100° C. or in an inert organic solvent in the presence of hydrogen and a customary hydrogenation catalyst, for example a noble metal catalyst, such as palladium on carbon or an alkaline earth metal carbonate, or platinum oxide, or Raney nickel, at room temperature and normal pressure or at moderately elevated temperatures and pressures. When using aldehydes, especially formaldehyde, more especially in the presence of formic acid, all the hydrogen atoms present are replaced by lower alkyl, for example methyl, whilst when using ketones in the presence of hydrogen and hydrogenation catalysts, it is possible to obtain also compounds of the general formula I in which $R_1$ is secondary lower alkyl and $R_2$ is hydrogen.

The compounds of the general formula II are also novel substances. For the manufacture of those compounds in which Ar represents a benzo radical and $R_5$ represents hydrogen, whilst $R_3$ and $R_4$ have the meanings given under formula I, it is possible to use as starting materials, for example, o-nitroanilines that are substituted in the amino group optionally in a manner corresponding to the definition of $R_3$ and optionally substituted in the benzene ring. There is first introduced into their amino group a suitable protecting group, such as a lower alkoxycarbonyl group, for example the ethoxycarbonyl group, by the successive action of sodium hydride and chloroformic acid ethyl ester in dimethylformamide, and in the resulting product the nitro group is reduced to an amino group in customary manner, for example by means of hydrogen in the presence of Raney nickel. The reduction product is converted into the corresponding diazonium chloride by dissolution in a hydrochloric acid/acetic acid mixture and the addition of sodium nitrite solution, and the diazonium chloride is then coupled with a (2-chloro-lower alkaneamido)-malonic acid di-lower alkyl ester, such as the diethyl ester, to form the corresponding azo compound, for example the corresponding [2-(N-alkoxycarbonyl-N-$R_3$-amino)-phenylazo]-(2-chloro-lower alkaneamido)-malonic acid diethyl ester. By treating the latter with aqueous sodium hydroxide solution at room temperature and acidifying, for example with hydrochloric acid at low temperature, there is produced after hydrolysis, decarboxylation and subsequent condensation, the corresponding 1-[2-(N-ethoxycarbonyl-N-$R_3$-amino)-phenyl]-5-(1-chloro-lower alkyl)-1H-1,2,4-triazole-3-carboxylic acid which, in turn, is cyclised with the removal of the ethoxycarbonyl group, for example by means of concentrated hydrobromic acid, at elevated temperature, for example at approximately 90° C., to form the corresponding 4-$R_4$-5-$R_3$-4,5-dihydro[1,2,4]triazolo[1,5-a]quinoxaline-2-carboxylic acid. This may contain substituents in the benzene ring, that is to say in one of the positions 6, 7, 8 and 9, provided that there was used as starting material an N-$R_3$-2-nitroaniline correspondingly substituted in the benzene ring. Finally, the resulting carboxylic acid can, either directly or after esterification, for example conversion into the methyl ester by boiling with methanol and hydrochloric acid, be reduced by means of a hydride reducing agent, for example treatment with sodium borohydride in a mixture of methanol and tetrahydrofuran, to form the corresponding 4-$R_4$-5-$R_3$-4,5-dihydro[1,2,4]triazolo[1,5-a]quinoxaline-2-methanol of the general formula II. The latter can be converted in customary manner into the reactive ester desired for the reaction according to (a), for example by reaction with methanesulphonyl chloride in the presence of a suitable base, for example triethylamine, in an inert organic solvent into the corresponding methanesulphonic acid ester, or by reaction with phosphorus tribromide in an inert organic solvent into the corresponding bromide, that is to say the corresponding 2-(bromomethyl) compound.

Compounds of the general formula II in which Ar represents a pyrido radical can be manufactured in analogous manner, but those compounds in which Ar represents a pyrido[2,3-e] radical and which are substituted neither in the 7-position nor in the 9-position by chlorine or bromine, are usually obtained more advantageously by the following reaction sequence using as starting material 3-amino-2-chloropyridine that is optionally substituted in the 4- or 6-position but not by chlorine and especially not by bromine. The mentioned amino compound is converted in customary manner into the correponding diazonium chloride and the latter is coupled with a (2-chloro-lower alkaneamido)-malonic acid di-lower alkyl ester, such as the diethyl ester or dimethyl ester, to form corresponding (2-chloro-lower alkaneamido)-(2-chloro-3-pyridylazo)-malonic acid di-lower alkyl ester. This is converted into the corresponding 1-(2-chloro-3-pyridyl)-5-(1-chloro-lower alkyl)-1H-1,2,4-triazole-3-carboxylic acid by successive treatment with aqueous/alkanolic sodium hydroxide solution at room temperature and with hydrochloric acid at low temperature. The latter compound is converted by reaction with ammonia or a primary amine of the formula $R_3$—$NH_2$, optionally in the presence of an amount ranging from a catalytic amount to double the molar amount of an alkali metal iodide, into the corresponding 4-$R_4$-5-$R_3$-4,5-dihydropyrido[2,3-b]-[1,2,4]triazolo[1,5-d]pyrazine-2-carboxylic acid and the latter is reduced analogously to the above-mentioned reaction sequence, preferably after esterification, to form the corresponding compound of the general formula II and this is converted into a suitable reactive ester.

Compounds of the general formula II in which both $R_4$ and $R_5$ represent lower alkyl, especially methyl, are obtained, for example, by not immediately reducing an ester obtained in the above-mentioned reaction sequences as a direct precursor to the hydroxy compound of the general formula II, for example a methyl ester, in which $R_4$ represents lower alkyl, especially methyl, but first converting it, for example by means of lithium diisopropylamide, into the corresponding alkali metal compound, and then reacting the latter with a lower alkyl halide, such as methyl iodide, and only subsequently reducing the ester group to form the hydroxymethyl group.

The starting materials of the general formula IV in which $X_1$ represents oxygen and n represents 0 for the reduction according to method (b) are also novel. They can be manufactured in a manner known per se from the corresponding above-mentioned carboxylic acids or the functional derivatives thereof, for example the lower alkyl esters also already mentioned or, for example, also the corresponding acid chlorides, by reaction with amines of the general formula III. Those starting materials of the general formula IV in which $R_4$ and $R_5$ each represent lower alkyl, especially methyl, are preferably manufactured from corresponding compounds in which $R_4$ is lower alkyl and $R_5$ is hydrogen by the introduction of lower alkyl $R_5$ analogously to the above-mentioned introduction of lower alkyl $R_5$ into the esters corresponding to the amides of the general formula IV. Compounds of the general formula IV in which X represents two hydrogen atoms and n represents 1 are obtained from compounds of the general formula I in which $R_1$ and optionally also $R_2$ represent(s) hydrogen, by the introduction of a lower alkanoyl, hydroxy-lower alkanoyl or lower alkoxycarbonyl radical, for example by reaction with a lower alkyl ester of the corresponding lower alkanoic acid or hydroxy-lower alkanoic acid or with a lower alkanoyl chloride or chloroformic acid lower alkyl ester.

Depending upon the starting materials and methods chosen, the novel compounds may be in the form of one of the possible stereoisomers or a mixture thereof, for example, according to the number of centres of asymmetry, in the form of pure optical isomers, that is to say optical antipodes or in the form of racemates, and in the case of diastereoisomerism, also in the form of racemic mixtures.

Resulting racemic mixtures can be separated in known manner into the pure racemates on the basis of the physico-chemical differences between the constituents, for example by means of chromatography and/or fractional crystallisation.

Resulting racemates can be resolved into the optical antipodes by known methods, for example by recrystallisation from an optically active solvent, with the aid of microorganisms or by reacting an end product with an optically active acid that forms salts with the racemic base and separating the salts obtained in this manner, for example on the basis of their different solubilities, into the diastereoisomers from which the antipodes can be freed by the action of suitable agents. Advantageously, the more active of the two antipodes is isolated.

Resulting free compounds of the formula I can be converted into acid addition salts in a manner known per se, inter alia by treatment with the corresponding acid, customarily in the presence of a solvent or diluent.

Resulting acid addition salts can be converted into the free compounds in a manner known per se, for example by treatment with a base, such as an alkali metal hydroxide or a basic ion exchanger.

The compounds, including their salts, can also be obtained in the form of their hydrates or can include the solvent used for crystallisation.

The invention relates also to those embodiments of the process according to which a compound obtainable as an intermediate at any stage of the process is used as starting material and the remaining steps are carried out or an optical antipode is used as starting material instead of a racemate, and/or a starting material is used in the form of a salt or, especially, is formed under the reaction conditions.

In the process of the present invention it is preferable to use those starting materials which result in the compounds described at the beginning as being especially valuable. The present invention relates also to novel starting materials and to processes for their manufacture.

The pharmaceutical preparations according to the invention contain, for example, from approximately 10% to approximately 95%, preferably from approximately 20% to approximately 90%, of at least one active ingredient according to the invention together with at least one pharmaceutical carrier or adjunct. Pharmaceutical preparations according to the invention are, for example, those in dosage unit forms, such as dra ees, tablets, capsules or suppositories, and also ampoules. Such preparations contain, per dosage unit, for example, from 10 to 500 mg, preferably from 25 to 250 mg, of active ingredient.

The pharmaceutical preparations of the present invention are manufactured in a manner known per se, for example by means of conventional mixing, granulating, confectioning, dissolving and lyophilising processes.

For example, pharamaceutical preparations for oral use can be obtained by combining the active ingredient with solid carriers, optionally granulating a resulting mixture and processing the mixture or granulate, if desired or necessary after the addition of suitable adjuncts, to form tablets or dra ee cores. Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, maize, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dra ee cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dra ee coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and, optionally, also stabilisers.

The invention relates also to a method for treating conditions of depression or anxiety in a mammal, including a human being, comprising administering to said mammmal a therapeutically effective amount of a compound of the general formula I or of a pharmaceutically acceptable acid addition salt thereof as an antidepressive or anxiolytic, preferably in the form of a pharmaceutical preparation. The dosage depends upon the species of mammal, the age and individual condition of the mammal to be treated and upon the method of administration. The daily doses administered are between approximately 1 and approximately 100 mg/kg and preferably, for example for mammals, including human beings, of approximately 70 kg body weight, between approximately 3 and approximately 50 mg/kg.

The following Examples illustrate the invention described above but are not intended to limit the scope thereof in any way. Temperatures are given in degrees Centigrade.

EXAMPLE 1

At −10° under nitrogen, 3.10 g (0.027 mol) of methanesulphonic acid chloride are added dropwise over a period of 5 minutes to a suspension of 5.00 g (0.018 mol) of 5-phenyl-4,4-dihydro-[1,2,4]-triazolo[1,5-a]quinoxaline-2-methanol in 180 ml of absolute methylene chloride and 3.64 g (0.036 mol) of triethylamine. After stirring for 1 hour at 0°, there are added a further 0.70 g of triethylamine and 0.60 g of methanesulphochloride, stirring is continued at 0° for 30 minutes and the clear reaction solution is completely concentrated by evaporating in vacuo at 35°, the methanesulphonic acid ester of 5-phenyl-4,5-dihydro-[1,2,4]triazolo[1,5-a]quinoxaline-2-methanol being obtained in the form of a colourless crystalline residue (contains triethylamine hydrochloride). The methanesulphonic acid ester so obtained is immediately reacted further, without further purification, by adding an ice-cold mixture of 15.0 ml (0.11 mol) of 33% ethanolic dimethylamine solution and 15 ml of ethanol and stirring the reaction mixture in a closed container for one hour. The mixture is then concentrated by evaporation in vacuo and the residue is dissolved in ethyl acetate and 1N potassium bicarbonate solution. The aqueous phase is separated off and extracted twice more with ethyl acetate. The combined organic extracts are washed three times with water and once with saturated sodium chloride solution and dried over sodium sulphate. After filtering off the drying agent, ethereal hydrogen chloride solution is added dropwise to the filtrate, while stirring well, until a pH value of 4 has been reached. After stirring for 3 hours in an ice bath, the crude hydrochloride that has formed is filtered off and washed with ethyl acetate. It is then dissolved in 70 ml of methylene chloride and 100 ml of isopropanol. After evaporating off the methylene chloride in vacuo at 40°, the desired hydrochloride crystallises out again. It is left to stand in a refrigerator for approximately 15 hours and the crystals are filtered off and washed with isopropanol. After drying under a high vacuum at 120°, the resulting 2-[(dimethylamino)-methyl]-5-phenyl-4,5-dihydro-[1,2,4]triazolo[1,5-a]quinoxaline hydrochloride of the formula

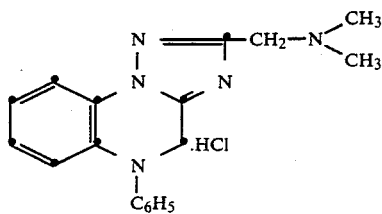

melts at 232°–235° with decomposition.

The 5-phenyl-4,5-dihydro-[1,2,4]-triazolo[1,5-a]quinoxaline-2-methanol required as starting material is manufactured as follows:

(a) While stirring well at 10°–15° under nitrogen, a solution of 79.40 g (0.371 mol) of o-nitrodiphenylamine [cf. F. Kehrmann and E. Havas, Ber. 46, 341 (1913)] in 500 ml of dimethylformamide is added dropwise, over a period of one hour, to a suspension of 19.60 g (approximately 0.41 mol) of sodium hydride/mineral oil in 100 ml of dimethylformamide. The reaction mixture is stirred for a further three hours at room temperature and then 45.0 ml (0.472 mol) of chloroformic acid ethyl ester are added dropwise at 20°. After stirring for one hour at room temperature, the reaction mixture is cooled to 0° and 15 ml of glacial acetic acid are slowly added dropwise thereto, the pH value finally being 5. The reaction mixture is then poured onto a mixture of ice and water and is extracted three times with ethylacetate. The extracts are washed three times with water and twice with saturated sodium chloride solution, dried over sodium sulphate and concentrated to dryness by evaporation in vacuo. The residue is stirred with 200 ml of hexane and 100 ml of water for three hours. The crude product that crystallises out is filtered off and washed well with water and hexane. After recrystallisation from isopropanol, (2-nitrophenyl)-phenylcarbamic acid ethyl ester having a melting point of 53°–56° is obtained.

(b) A solution of 35.15 g (0.123 mol) of (2-nitrophenyl)-phenylcarbamic acid ethyl ester in 350 ml of ethanol, with the addition of 8.0 g of Raney nickel, is hydrogenated at normal pressure for 25 hours at 15°–20°. After filtering off the catalyst, the filtrate is concentrated by evaporation in vacuo at a maximum of 40° and the residue is recrystallised from methylene chloride/hexane. After drying in vacuo, the resulting N-(2-aminophenyl)-phenylcarbamic acid ethyl ester melts at 87°–90°.

(c) A solution of 34.00 g (0.133 mol) of (2-aminophenyl)-phenylcarbamic acid ethyl ester in 319 ml of glacial acetic acid and 80 ml of concentrated hydrochloric acid is diazotised at 0°–5° with 27 ml (0.133 mol) of a 5 molar sodium nitrite solution. 80 g of ice are then added to the resulting diazonium salt solution and then a solution of 33.40 g (0.133 mol) of (2-chloroacetamido)-malonic acid diethyl ester [cf. Ajay Kumar Bose, J. Indian Chem. Soc. 31, 108–110 (1954)] in 330 ml of acetone are added quickly dropwise. 610 ml of a saturated potassium carbonate solution are then added dropwise at 0°–5° over a period of 30 minutes, the pH value of the reaction mixture finally being 6. After the addition of 50 ml of ether, the mixture is stirred in an ice bath for 90 minutes and then the reaction product, which has already crystallised out, is filtered. The crystals are washed well with water and a small quantity of ether. After drying over calcium chloride in a dessicator, the resulting [2-(N-ethoxycarbonylphenylamino)-phenylazo]-(2-chloroacetamido)-malonic acid diethyl ester melts at 102°–104°. In order to obtain more reaction product the combined filtrates are extracted with 500 ml of ethyl acetate. The separated organic phase is separated off, washed four times with water and once with saturated sodium chloride solution, dried over sodium sulphate and concentrated by evaporation in vacuo. The residue is dissolved in 50 ml of ether and, for the purpose of crystallisation, is left to stand in a closed container for two days at room temperature. The crystals that have formed are then filtered off and washed with a small quantity of ether and a large quantity of hexane. After drying, the same product is obtained in a quantity greater than that obtained directly. Melting point 102°–104°.

(d) While stirring well, a solution of 146.6 g (0.283 mol) of the azo compound prepared according to (c) in 1466 ml of methanol is added over a period of 5 minutes to 848 ml (0.848 mol) of a 1N sodium hydroxide solution pre-cooled to 0°. The mixture is stirred at room temperature for 90 minutes and then, while cooling with a mixture of ice and water, 450 ml of 2N hydrochloric acid are added dropwise until the mixture is acidic to Congo red. The free carboxylic acid crystallises out after inoculation and trituration with a glass rod. The resulting crystal mass is stirred at 0° for 3 hours, then filtered with suction, washed with water until pH 5 and dried in vacuo at 80° over calcium chloride. The resulting 1-[2-(N-ethoxycarbonylphenylamino)-phenyl]-5-(chloromethyl)-1H-1,2,4-triazole-3-carboxylic acid sinters at 158° and melts at 167°–170° with decomposition.

(e) A suspension of 53.80 g (0.134 mol) of the carboxylic acid prepared according to (d) in 280 ml of 48% hydrobromic acid is stirred under nitrogen for 22 hours at a bath temperature of 105°, there first being produced a clear solution and then a crystalline precipitate gradually appearing after two hours. The reaction mixture is then cooled to room temperature and, while stirring, 300 ml of water are added. After cooling at 0° for 3 hours, the carboxylic acid is filtered with suction, washed with a total of 800 ml of water to pH 5 and dried in vacuo, first over calcium chloride and then over phosphorus pentoxide. The resulting 5-phenyl-4,5-dihydro-[1,2,4]triazolo[1,5-a]quinoxaline-2-carboxylic acid melts at 205°–207° with decomposition.

(f) A suspension of 74.90 g (0.256 mol) of the carboxylic acid prepared according to (e) in 1500 ml of methanol and 300 ml of 6N methanolic hydrochloric acid solution is stirred under nitrogen under reflux at boiling temperature for 17 hours, a clear solution being obtained after one hour. The reaction mixture is then stirred at 0° for 4 hours and the crystals that are formed are filtered with suction and washed with a total of 250 ml of methanol. After drying over calcium chloride and potassium hydroxide in vacuo, the resulting 5-phenyl-4,5-dihydro-[1,2,4]triazolo[1,5-a]quinoxaline-2-carboxylic acid methyl ester sinters at 140° and melts at 150°–154°.

(g) While stirring under nitrogen, a total of 30 g (0.794 mol) of sodium borohydride, divided into three portions, are added at room temperature over a period of 15 minutes to a suspension of 87.0 g (0.285 mol) of the ester prepared according to (f) in 870 ml of methanol and 870 ml of tetrahydrofuran. The reaction mixture foams vigorously and its temperature rises to 30°, and that temperature is maintained by cooling with cold water. Stirring is continued at room temperature for 2 hours and, after the addition of 1750 ml of a mixture of ice and water, for a further 3 hours at 0°. The alcohol that is precipitated is filtered with suction and washed with water to pH 6. After drying over calcium chloride in vacuo, the resulting 5-phenyl-4,5-dihydro-[1,2,4]triazolo[1,5-a]quinoxaline-2-methanol melts at 180°–185°.

EXAMPLE 2

The crude methanesulphonic acid ester prepared according to Example 1 from 8.70 g (0.0313 mol) of 5-phenyl-4,5-dihydro-[1,2,4]triazolo[1,5-a]quinoxaline-2-methanol and 5.92 g (0.051 mol) of methanesulphonic acid chloride is stirred for 1 hour at room temperature after the addition of 24 ml (0.188 mol) of 33% ethanolic methylamine solution and 24 ml of ethanol. The reaction mixture is then concentrated by evaporation in vacuo and the residue is dissolved in ethyl acetate and 1N potassium bicarbonate solution. The aqueous phase is separated off and extracted twice more with ethyl acetate. The combined organic extracts are washed three times with water and once with saturated sodium chloride solution, dried over sodium sulphate and concentrated to dryness by evaporation in vacuo.

The 9.20 g of residue are dissolved in methylene chloride/methanol (9:1) and the solution is chromatographed over a column of 900 g of silica gel. Methylene chloride/methanol (9:1) is again used, as eluant. The fractions that contain the desired crude product having an $R_f$ value of 0.4 [system:methylene chloride/methanol (9:1)] are concentrated to dryness by evaporation and dissolved in 30 ml of acetone, and a solution of oxalic acid in acetone is added until a pH value of 6 has been reached. The solution is left to stand at room temperature for approximately 15 hours and the crystals that have formed are filtered off and washed with acetone. After drying under a high vacuum at 90°, the resulting 2-[(methylamino)methyl]-5-phenyl-4,5-dihydro-[1,2,4]triazolo[1,5-a]quinoxaline oxalate sinters at 190° and melts at 210°–213°.

EXAMPLE 3

A suspension of 22.50 g (0.066 mol) of 2-(bromomethyl)-5-phenyl-4,5-dihydro-[1,2,4]triazolo[1,5-a]quinoxaline in 225 ml of isopropanol and 45.30 ml (0.33 mol) of 33% ethanolic dimethylamine solution is stirred under nitrogen at room temperature for two hours. The mixture is then concentrated by evaporation in vacuo and the residue is dissolved in ethyl acetate and 1N potassium bicarbonate solution. The aqueous phase is separated off and extracted twice more with ethyl acetate. The combined organic extracts are washed three times with water and once with saturated sodium chloride solution and dried over sodium sulphate. The drying agent is filtered off and, while stirring well, ethereal hydrogen chloride solution is added dropwise to the filtrate until a pH value of 4 has been reached. After stirring for 3 hours in an ice bath, the crude hydrochloride that has formed is filtered off and washed with ethyl acetate. Recrystallisation as described in Example 1 yields 2-[(dimethylamino)-methyl]-5-phenyl-4,5-dihydro-[1,2,4]triazolo[1,5-a]quinoxaline hydrochloride having a melting point of 232°–235° with decomposition.

In analogous manner, from 10.0 g (0.029 mol) of the same bromomethyl compound there is obtained with 10.70 g (0.146 mol) of diethylamine, 2-[(diethylamino)-methyl]-5-phenyl-4,5-dihydro-[1,2,4]triazolo[1,5-a]quinoxaline hydrochloride having a melting point of 192°–195° (with decomposition) after crystallisation from methylene chloride/ethyl acetate, and with 12.40 g (0.146 mol) of piperidine there is obtained 2-[(piperidino)-methyl]-5-phenyl-4,5-dihydro-[1,2,4]triazolo[1,5-a]quinoxaline hydrochloride having a melting point of 240°–250° (with decomposition) after crystallisation from methylene chloride/ethyl acetate.

The 2-(bromomethyl)-5-phenyl-4,5-dihydro-[1,2,4]triazolo[1,5-a]quinoxaline required as starting material is prepared as follows:

(a) At 20° under nitrogen, 43.00 g (0.159 mol) of phosphorus tribromide are added dropwise over a period of 30 minutes to a suspension of 44.30 g (0.159 mol) of the 5-phenyl-4,5-dihydro-[1,2,4]triazolo[1,5-a]quinoxaline-2-methanol prepared according to Example 1 (g) in 660 ml of absolute methylene chloride and the mixture is stirred at room temperature for a further 4 hours. The mixture is then concentrated to dryness by evaporation in vacuo at 40° and the residue is dissolved in 1200 ml of ethyl acetate and 200 ml of a mixture of ice and water. The aqueous phase is separated off and extracted once more with ethyl acetate. The combined organic extracts are washed 4 times with water and once with saturated sodium chloride solution, dried over sodium sulphate and concentrated to dryness by evaporation in vacuo. The crystalline residue is dissolved in 200 ml of methylene chloride and 500 ml of isopropanol. After evaporating off the methylene chloride in vacuo at 40°, the desired compound crystallises out. The crystal mass is left to stand in a refrigerator for approximately 15 hours and the crystals are filtered off and washed with isopropanol. After drying over calcium chloride in a vacuum desiccator, the resulting 2-(bromomethyl)-5-phenyl-4,5-dihydro-[1,2,4]triazolo[1,5-a]quinoxaline sinters from 115° and melts at 122°–130°.

EXAMPLE 4

At 2° under nitrogen, 9.40 ml (0.011 mol) of a 1.2 molar solution of diisobutylaluminium hydride in toluene are added dropwise, over a period of 15 minutes, to a suspension of 1.20 g (0.0037 mol) of N,N-dimethyl-5-phenyl-4,5-dihydro-[1,2,4]triazolo[1,5-a]quinoxaline-2-carboxamide in 180 ml of absolute toluene. The resulting clear yellow solution is stirred at 5° for a further hour and then 5 ml of isopropanol are added dropwise to the reaction mixture and the whole is poured onto a mixture of ice and water. The organic phase is separated off, washed twice with ice-water and once with saturated sodium chloride solution, dried over sodium sulphate and concentrated by evaporation in vacuo. The honey-like residue is dissolved in 20 ml of ethyl acetate and, while stirring well, ethereal hydrogen chloride solution is slowly added dropwise until a pH value of 4 has been reached. After leaving to stand in a refrigerator for approximately 15 hours, the crude hydrochloride is filtered off and washed with ethyl acetate. Recrystallisation as described in Example 1 yields 2-[(dimethylamino)-methyl]-5-phenyl-4,5-dihydro[1,2,4]-triazolo[1,5-a]quinoxaline hydrochloride having a melting point of 232°-235° with decomposition.

The carboxamide required as starting material is prepared as follows:

(a) A mixture of 7.00 g (0.023 mol) of the 5-phenyl-4,5-dihydro-[1,2,4]triazolo[1,5-a]quinoxaline-2-carboxylic acid methyl ester prepared according to Example 1(f) in 300 ml of methanol and 62.6 ml (0.457 mol) of 33% ethanolic dimethylamine solution is heated at 100° in an autoclave for 16 hours. The reaction mixture is then concentrated by evaporation in vacuo and the residue is dissolved in methylene chloride and a mixture of ice and water. The organic phase is washed twice with cold 5% potassium bicarbonate solution and once with saturated sodium chloride solution, dried over sodium sulphate and concentrated by evaporation in vacuo. The amorphous residue crystallises when triturated with 300 ml of ether. After filtration and drying in a high vacuum, there is obtained N,N-dimethyl-5-phenyl-4,5-dihydro-[1,2,4]triazolo[1,5-a]quinoxaline-2-carboxamide which sinters from 125° and gradually melts at 150°-165°.

EXAMPLE 5

In a manner analogous to that described in Example 1, using as starting material 9.30 g (0.0297 mol) of 5-(4-chlorophenyl)-4,5-dihydro-[1,2,4]triazolo[1,5-a]quinoxaline-2-methanol there is obtained via the crude methanesulphonic acid ester thereof using 40.7 ml (0.297 mol) of 33% ethanolic dimethylamine solution, 2-[(dimethylamino)methyl]-5-(4-chlorophenyl)-4,5-dihydro-[1,2,4]triazolo[1,5-a]quinoxaline hydrochloride which, after recrystallisation from methylene chloride/isopropanol, sinters at 230° and melts at 248°-251° with decomposition.

In a manner analogous to that described in Example 1, using as starting material 20.30 g (0.059 mol) of 5-[3-(trifluoromethyl)-phenyl]-4,5-dihydro-[1,2,4]triazolo[1,5-a]quinoxaline-2-methanol there is obtained via the crude methanesulphonic acid ester thereof using 48.2 ml (0.35 mol) of 33% ethanolic dimethylamine solution, 2-[(dimethylamino)-methyl]-5-[3-(trifluoromethyl)-phenyl]-4,5-dihydro-[1,2,4]triazolo[1,5-a]quinoxaline which, for purification, is chromatographed over basic aluminium oxide of activity stage I using methylene chloride/methanol (99:1) as eluant, and then recrystallised from hexane. The product (free base) melts at 115°-118°.

In a manner analogous to that described in Example 1, using as starting material 35.05 g (0.144 mol) of 5-(2,3-dimethylphenyl)-4,5-dihydro-[1,2,4]triazolo[1,5-a]quinoxaline-2-methanol there is obtained via the crude methanesulphonic acid ester thereof using 198 ml (1.44 mol) of 33% ethanolic dimethylamine solution, 2-[(dimethylamino)-methyl]-5-(2,3-dimethylphenyl)-4,5-dihydro-[1,2,4]triazolo[1,5-a]quinoxaline hydrochloride which, after recrystallisation from methylene chloride/isopropanol, sinters at 250° and melts at 257°-259° with decomposition.

In a manner analogous to that described in Example 1, using as starting material 8.0 g (0.026 mol) of 7-chloro-5-phenyl-4,5-dihydro-[1,2,4]triazolo[1,5-a]quinoxaline-2-methanol, there is obtained via the crude methanesulphonic acid ester thereof using 25.6 ml (0.218 mol) of 33% ethanolic dimethylamine solution, 7-chloro-2-[(dimethylamino)-methyl]-5-phenyl-4,5-dihydro-[1,2,4]triazolo[1,5-a]quinoxaline hydrochloride which, after recrystallisation from methylene chloride/ethyl acetate, sinters from 220° and melts at 228°-232° with decomposition.

In a manner analogous to that described in Example 1, using as starting material 16.50 g (0.0432 mol) of 8-chloro-5-(2,4-dichlorophenyl)-4,5-dihydro-[1,2,4]triazolo[1,5-a]quinoxaline-2-methanol there is obtained via the crude methanesulphonic acid ester thereof using 59.0 ml (0.432 mol) of 33% ethanolic dimethylamine solution, 8-chloro-2-[(dimethylamino)-methyl]-5-(2,4-dichlorophenyl)-4,5-dihydro-[1,2,4]triazolo[1,5-a]quinoxaline hydrochloride which, after recrystallisation from methylene chloride/isopropanol, melts from 282° with decomposition.

The methanol derivatives required as starting materials are prepared as follows:

(a) In a manner analogous to that described in Example (1a): using 26.2 g (0.105 mol) of 4-chloro-N-(2-nitrophenyl)-aniline [cf. V. C. Barry et al., *Proc. Roy. Irish Acad.*, 55B, 160 (1953)] there is obtained (4-chlorophenyl)-(2-nitrophenyl)-carbamic acid ethyl ester having a melting point of 90°-93° after recrystallisation from methylene chloride/hexane;

using 95.08 g (0.337 mol) of 2-nitro-N-[3-(trifluoromethyl)-phenyl]-aniline [cf. section (h) hereinafter] there is obtained (2-nitrophenyl)-[3-(trifluoromethyl)-phenyl]carbamic acid ethyl ester having a melting point of 45°-48° after recrystallisation from hexane;

using 65.0 g (0.268 mol) of 2,3-dimethyl-N-(2-nitrophenyl)-aniline [cf. section (h) hereinafter] there is obtained (2,3-dimethylphenyl)-(2-nitrophenyl)-carbamic acid ethyl ester having a melting point of 105°-106° after recrystallisation from isopropanol;

using 43.00 g (0.173 mol) of 5-chloro-2-nitro-N-phenylaniline [cf. A. P. Kottenhahn et al., *J. Org. Chem.* 28, 3117 (1963)] there is obtained, after chromatographing the crude product over silica gel using toluene as eluant, (5-chloro-2-nitrophenyl)-phenylcarbamic acid ethyl ester in the form of a brown oil which solidifies after a period of time and then melts at 71°-73°;

using 56.55 g (0.178 mol) of 2,4-dichloro-N-(2-nitrophenyl)-aniline [cf. V. C. Barry and J. G. Belton, *Proc. Roy. Irish Acad.*, 57B, 144 (1955)] there is obtained, after chromatographing the crude product over silica gel using toluene as eluant, (4-chloro-2-nitrophenyl)-(2,4-dichlorophenyl)-carbamic acid ethyl ester having a melting point of 93°–96° after recrystallisation from isopropanol.

(b) In a manner analogous to that described in Example (1b):

using 41.20 g (0.128 mol) of (4-chlorophenyl)-(2-nitrophenyl)-carbamic acid ethyl ester there is obtained (2-aminophenyl)-(4-chlorophenyl)-carbamic acid ethyl ester having a melting point of 112°–115° after recrystallisation from methylene chloride/hexane;

using 81.50 g (0.230 mol) of (2-nitrophenyl)-[3-(trifluoromethyl)-phenyl]-carbamic acid ethyl ester there is obtained (2-aminophenyl)-[3-(trifluoromethyl)-phenyl]-carbamic acid ethyl ester having a melting point of 105°–108° after recrystallisation from methylene chloride/hexane;

using 71.90 g (0.229 mol) of (2,3-dimethylphenyl)-(2-nitrophenyl)-carbamic acid ethyl ester there is obtained (2-aminophenyl)-(2,3-dimethylphenyl)-carbamic acid ethyl ester having a melting point of 95°–97° after recrystallisation from methylene chloride/hexane;

using 43.20 g (0.135 mol) of (5-chloro-2-nitrophenyl)-phenylcarbamic acid ethyl ester there is obtained (2-amino-5-chlorophenyl)-phenylcarbamic acid ethyl ester having a melting point of 98°–101° after recrystallisation from methylene chloride/hexane;

using 39.85 g (0.102 mol) of (2,4-dichlorophenyl)-(4-chloro-2-nitrophenyl)-carbamic acid ethyl ester there is obtained (2-amino-4-chlorophenyl)-(2,4-dichlorophenyl)-carbamic acid ethyl ester having a melting point of 137°–139° after recrystallisation from methylene chloride/hexane.

(c) In a manner analogous to that described in Example (1c): using 38.60 g (0.133 mol) of (2-aminophenyl)-(4-chlorophenyl)-carbamic acid ethyl ester there is obtained [2-(N-ethoxycarbonyl-4-chlorophenylamino)-phenylazo]-(2-chloroacetamido)-malonic acid diethyl ester having a melting point of 80°–85° after recrystallisation from ether/hexane; using 61.20 g (0.189 mol) of (2-aminophenyl)-[3-(trifluoromethyl)-phenyl]-carbamic acid ethyl ester there is obtained [2-[N-ethoxycarbonyl-3-(trifluoromethyl)-phenylamino]-phenylazo]-(2-chloroacetamido)-malonic acid diethyl ester having a melting point of 76°–79° after recrystallisation from ether/hexane;

using 56.60 g (1.199 mol) of (2-aminophenyl)-(2,3-dimethylphenyl)-carbamic acid ethyl ester there is obtained [2-(N-ethoxycarbonyl-2,3-dimethylphenylamino)-phenylazo]-(2-chloroacetamido)-malonic acid diethyl ester having a melting point of 120°–122° after recrystallisation from ether/hexane;

using 31.60 g (0.109 mol) of (2-amino-5-chlorophenyl)-phenylcarbamic acid ethyl ester there is obtained [2-(N-ethoxycarbonylphenylamino)-4-chlorophenylazo]-(2-chloroacetamido)-malonic acid diethyl ester which, after crystallisation from ether, sinters from 90° and melts at 105°–110°;

using 33.30 g (0.093 mol) of (2-amino-4-chlorophenyl)-(2,4-dichlorophenyl)-carbamic acid ethyl ester there is obtained amorphous [2-(N-ethoxycarbonyl-2,4-dichlorophenylamino)-5-chlorophenylazo]-(2-chloroacetamido)-malonic acid diethyl ester. This crude malonic ester can be used directly for cyclisation in a manner analogous to Example (1d).

(d) In a manner analogous to that described in Example (1d): using 36.90 g (0.067 mol) of [2-(N-ethoxycarbonyl-4-chlorophenylamino)-phenylazo]-(2-chloroacetamido)-malonic acid diethyl ester there is obtained crude 1-[2-(N-ethoxycarbonyl-4-chlorophenylamino)-phenyl]-5-(chloromethyl)-1H-1,2,4-triazole-3-carboxylic acid which sinters at 185° and melts at 190°–192° with decomposition;

using 98.50 g (0.168 mol) of [2-(N-ethoxycarbonyl-3-(trifluoromethyl)-phenylamino)-phenylazo]-(2-chloroacetamido)-malonic acid diethyl ester there is obtained crude 1-[2-[N-ethoxycarbonyl-3-(trifluoromethyl)-phenylamino]-phenyl]-5-(chloromethyl)-1H-1,2,4-triazole-3-carboxylic acid which sinters from 88° and melts at 100°–108° with decomposition; using 91.10 g (0.166 mol) of [2-(N-ethoxycarbonyl-2,3-dimethylphenylamino)-phenylazo]-(2-chloroacetamido)-malonic acid diethyl ester there is obtained crude 1-[2-(N-ethoxycarbonyl-2,3-dimethylphenylamino)-phenyl]-5-(chloromethyl)-1H-1,2,4-triazole-3-carboxylic acid which melts at 188°–190° with decomposition;

using 53.70 g (0.097 mol) of [2-(N-ethoxycarbonylphenylamino)-4-chlorophenylazo]-(2-chloroacetamido)-malonic acid diethyl ester there is obtained crude 1-[2-(N-ethoxycarbonylphenylamino)-4-chlorophenyl]-5-(chloromethyl)-1H-1,2,4-triazole-3-carboxylic acid which sinters at 105° and melts at 115°–117° with decomposition;

using 59.53 g (0.0957 mol) of crude [2-(N-ethoxycarbonyl-2,4-dichlorophenylamino)-5-chlorophenylazo]-(2-chloroacetamido)-malonic acid diethyl ester there is obtained crude 1-[2-(N-ethoxycarbonyl-2,4-dichlorophenylamino)-5-chlorophenyl]-5-(chloromethyl)-1H-1,2,4-triazole-3-carboxylic acid which melts at 186° with decomposition.

(e) In a manner analogous to that described in Example (1e):

using 50.00 g (0.115 mol) of crude 1-[2-(N-ethoxycarbonyl-4-chlorophenylamino)-phenyl]-5-(chloromethyl)-1H-1,2,4-triazole-3-carboxylic acid there is obtained crude 5-(4-chlorophenyl)-4,5-dihydro-[1,2,4]triazolo[1,5-a]quinoxaline-2-carboxylic acid which sinters at 191° and melts from 196° with decomposition;

using 77.50 g (0.165 mol) of crude 1-[2-[N-ethoxycarbonyl-3-(trifluoromethyl)-phenylamino]-phenyl]-5-(chloromethyl)-1H-1,2,4-triazole-3-carboxylic acid there is obtained crude 5-[3-(trifluoromethyl)-phenyl]-4,5-dihydro-[1,2,4]triazolo[1,5-a]quinoxaline-2-carboxylic acid which melts at 204°–206° with decomposition;

using 69.70 g (0.163 mol) of crude 1-[2-(N-ethoxycarbonyl-2,3-dimethylphenylamino)-phenyl]-5-(chloromethyl)-1H-1,2,4-triazole-3-carboxylic acid there is obtained crude 5-(2,3-dimethylphenyl)-4,5-dihydro-[1,2,4]triazolo[1,5-a]quinoxaline-2-carboxylic acid which sinters at 178° with red coloration and melts at 195°–197° with decomposition;

using 42.20 g (0.097 mol) of crude 1-[2-(N-ethoxycarbonylphenylamino)-4-chlorophenyl]-5-(chloromethyl)-1H, 1,2,4-triazole-3-carboxylic acid there is obtained crude 7-chloro-5-phenyl-4,5-dihydro-[1,2,4]triazolo[1,5-a]quinoxaline-2-carboxylic acid which sinters at 178° with brown coloration and melts at 205°–210° with decomposition;

using 33.30 g (0.066 mol) of crude 1-[2-(N-ethoxycarbonyl-2,4-dichlorophenylamino)-5-chlorophenyl]-5-(chloromethyl)-1H-1,2,4-triazole-3-carboxylic acid there is obtained crude 8-chloro-5-(2,4-dichlorophenyl)-4,5-dihydro-[1,2,4]triazolo[1,5-a]quinoxaline-2-carboxylic acid which melts at 218°–222° with decomposition.

(f) In a manner analogous to that described in Example (1f): using 43.40 g (0.133 mol) of crude (5-(4-chlorophenyl)-4,5-dihydro-[1,2,4]triazolo[1,5-a]quinoxaline-2- carboxylic acid there is obtained 5-(4-chlorophenyl)-4,5-dihydro-[1,2,4]triazolo[1,5-a]quinoxaline-2-carboxylic acid methyl ester which, after recrystallisation from methylene chloride/isopropanol sinters at 143° and melts at 155°–212° with gradual decomposition;

using 54.10 g (0.150 mol) of crude 5-[3-(trifluoromethyl)-phenyl]-4,5-dihydro-[1,2,4]triazolo[1,5-a]quinoxaline-2-carboxylic acid there is obtained 5-[3-(trifluoromethyl)-phenyl]-4,5-dihydro-[1,2,4]triazolo[1,5-a]quinoxaline-2-carboxylic acid methyl ester which, after recrystallisation from methylene chloride/methanol, melts at 204°–206°;

using 58.10 g (0.181 mol) of crude 5-(2,3-dimethylphenyl)-4,5-dihydro-[1,2,4]triazolo[1,5-a]quinoxaline-2-carboxylic acid there is obtained 5-(2,3-dimethylphenyl)-4,5-dihydro-[1,2,4]triazolo[1,5-a]quinoxaline-2-carboxylic acid methyl ester which, after recrystallisation from methylene chloride/methanol, melts at 170°–172°;

using 26.60 g (0.0815 mol) of crude 7-chloro-5-phenyl-4,5-dihydro-[1,2,4]triazolo[1,5-a]quinoxaline-2-carboxylic acid there is obtained 7-chloro-5-phenyl-4,5-dihydro-[1,2,4]triazolo[1,5-a]quinoxaline-2-carboxylic acid methyl ester which, after recrystallisation from methylene chloride/isopropanol, sinters at 165° and melts at 190°–194°;

using 25.40 g (0.0642 mol) of crude 8-chloro-5-(2,4-dichlorophenyl)-4,5-dihydro-[1,2,4]triazolo[1,5-a]quinoxaline-2-carboxylic acid there is obtained 8-chloro-5-(2,4-dichlorophenyl)-4,5-dihydro-[1,2,4]triazolo[1,5-a]quinoxaline-2-carboxylic acid methyl ester which, after recrystallisation from methylene chloride/isopropanol, melts at 264°–266°.

(g) In a manner analogous to that described in Example (1g):

using 38.50 g (0.113 mol) of 5-(4-chlorophenyl)-4,5-dihydro-[1,2,4]triazolo[1,5-a]quinoxaline-2-carboxylic acid methyl ester there is obtained 5-(4-chlorophenyl)-4,5-dihydro-[1,2,4]triazolo[1,5-a]quinoxaline-2-methanol which, after recrystallisation from methylene chloride/isopropanol, melts at 190°–195°;

using 26.65 g (0.0712 mol) of 5-[3-(trifluoromethyl)-phenyl]-4,5-dihydro-[1,2,4]triazolo[1,5-a]quinoxaline-2-carboxylic acid methyl ester there is obtained 5-[3-(trifluoromethyl)-phenyl]-4,5-dihydro-[1,2,4]-triazolo[1,5-a]quinoxaline-2-methanol which, after recrystallisation from methylene chloride/isopropanol, melts at 168°–171°;

using 39.84 g (0.119 mol) of 5-(2,3-dimethylphenyl)-4,5-dihydro-[1,2,4]triazolo[1,5-a]quinoxaline-2-carboxylic acid methyl ester there is obtained 5-(2,3-dimethylphenyl)-4,5-dihydro-[1,2,4]triazolo[1,5-a]quinoxaline-2-methanol which, after recrystallisation from methylene chloride/isopropanol, sinters at 165° and melts at 186°–194°;

using 20.80 g (0.061 mol) of 7-chloro-5-phenyl-4,5-dihydro-[1,2,4]triazolo[1,5-a]quinoxaline-2-carboxylic acid methyl ester there is obtained 7-chloro-5-phenyl-4,5-dihydro-[1,2,4]triazolo[1,5-a]quinoxaline-2-methanol which, after recrystallisation from methylene chloride/isopropanol, sinters at 191° and melts at 204°–207°;

using 19.80 g (0.0483 mol) of 8-chloro-5-(2,4-dichlorophenyl)-4,5-dihydro-[1,2,4]triazolo[1,5-a]quinoxaline-2-carboxylic acid methyl ester there is obtained 8-chloro-5-(2,4-dichlorophenyl)-4,5-dihydro-[1,2,4]triazolo[1,5-a]quinoxaline-2-methanol having a melting point of 229°–231°.

The two substituted 2-nitro-N-phenylanilines which are required for step (a) and are not described in the literature are manufactured as follows:

(h) A solution of 80.00 g (0.567 mol) of 1-fluoro-2-nitrobenzene and 182.72 g (1.133 mol) of 3-(trifluoromethyl)-aniline in 400 ml of dimethyl sulphoxide is stirred at 130° for 68 hours. After cooling, the reaction mixture is poured onto 1000 ml of water and extracted twice with 500 ml of ethyl acetate. The combined organic extracts are washed 5 times with 1N hydrochloric acid, 5 times with water and once with saturated sodium chloride solution, dried over sodium sulphate and concentrated by evaporation in vacuo. The oily residue is dissolved in 200 ml of toluene and the solution is filtered through an inflow flask filled with 610 g of silica gel, and the contents are then washed with 1000 ml of toluene. The filtrate is concentrated to dryness by evaporation in vacuo and the residue is recrystallised from methylene chloride/hexane. After drying in vacuo, the resulting 2-nitro-N-[3-(trifluoromethyl)-phenyl]-aniline melts at 69°–70°.

In an entirely analogous manner, using 117.00 g (0.830 mol) of 1-fluoro-2-nitrobenzene and 222.00 g (1.826 mol) of 2,3-dimethylaniline in 585 ml of dimethyl sulphoxide as starting materials there is obtained N-(2,3-dimethylphenyl)-2-nitroaniline having a melting point of 118°–120° after recrystallisation from methylene chloride/hexane.

EXAMPLE 6

At from −8° to −5°, 6.15 g (0.054 mol) of methanesulphonic acid chloride are added dropwise over a period of 10 minutes to a suspension of 10.00 g (0.0358 mol) of 5-phenyl-4,5-dihydropyrido[2,3-e][1,2,4]triazolo[1,5-a]pyrazine-2-methanol in 350 ml of absolute methylene chloride and 7.24 g (0.072 mol) of triethylamine. The clear yellow reaction solution is stirred at room temperature for a further 90 minutes and then washed three times with ice-water and once with saturated sodium chloride solution. The organic phase is dried over sodium sulphate and concentrated to dryness by evaporation in vacuo.

The methanesulphonic acid ester of 5-phenyl-4,5-dihydropyrido[2,3-e][1,2,4]triazolo[1,5-a]pyrazine-2-methanol is obtained in the form of a light-yellow crystalline residue and is immediately reacted further, without further purification, by adding an ice-cold mixture of 35.4 ml (0.26 mol) of 33% ethanolic dimethylamine solution and 35 ml of ethanol and stirring the reaction mixture in a closed container for 3 hours. The mixture is then concentrated by evaporation in vacuo and the residue is dissolved in ethyl acetate and 1N potassium bicarbonate solution. The aqueous phase is separated off and extracted twice more with ethyl acetate. The combined extracts are washed twice with water and once with saturated sodium chloride solution, dried over sodium sulphate and concentrated by evaporation in vacuo. After recrystallisation of the residue from methylene chloride/isopropanol, 2-[(dimethylamino)-methyl]-5-phenyl-4,5-dihydropyrido[2,3-e][1,2,4]triazolo[1,5-a]pyrazine is obtained which melts at 135°–139° and corresponds to the formula:

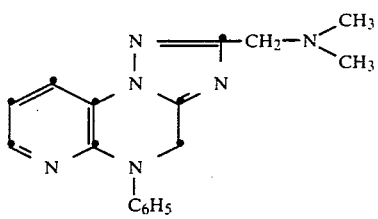

The 5-phenyl-4,5-dihydropyrido[2,3-e][1,2,4]-triazolo[1,5-a]pyrazine-2-methanol required as starting material is prepared as follows:

(a) A solution of 56.80 g (0.441 mol) of 3-amino-2-chloropyridine (purum) in 440 ml of glacial acetic acid and 110 ml of concentrated hydrochloric acid is diazotised at 0°–5° with 88.3 ml (0.441 mol) of a 5-molar sodium nitrite solution. While stirring well, the resulting still-cold diazonium salt solution is added dropwise over a period of 20 minutes to a solution of 88.50 g (0.353 mol) of (2-chloroacetamido)-malonic acid diethyl ester [cf. Ajay Kumar Bose, J. Indian Chem. Soc. 31, 108–110 (1954)] in 1760 ml of methanol while at the same time adding dropwise to the solution from a second dropping funnel 2400 ml of saturated potassium bicarbonate solution, while cooling gently, at such a rate that the pH value of the reaction mixture is always approximately 6 and the reaction temperature remains between 20° and 23°. There are then added dropwise a further 400 ml of saturated potassium bicarbonate solution (pH value reaches 7) and the whole is stirred for a further one hour at 20° and then for 2 hours at 0°–5°. The light yellow crystals that are formed are filtered with suction and washed with water, a small quantity of ether and, finally, with hexane. After drying in the air, the resulting (2-chloroacetamido)-(2-chloro-3-pyridylazo)-malonic acid diethyl ester, which contains varying amounts of water of crystallisation, melts at 60°–72°.

(b) While stirring well, a solution, cooled to 2°, of 118.30 g (approximately 0.27 mol) of the crude azo compound prepared according to (a) in 1060 mol of methanol is added over a period of 5 minutes to 817 ml (0.817 mol) of a 1N sodium hydroxide solution pre-cooled to 0°. While heating to 18°–20°, a clear reddish-brown solution is produced which is stirred at room temperature for a further 1 hour. 10 g of activated carbon are then added and the mixture is stirred at room temperature for 5 minutes and filtered through diatomaceous earth, subsequently washing with a small quantity of methanol/water (1:1). While stirring, 2N hydrochloric acid is added to the clear yellow filtrate until a pH value of 3 has been reached. After stirring for three hours in an ice bath, the acid that has crystallised out is filtered with suction and washed well with water and hexane. After drying over calcium chloride in vacuo, the resulting 1-(2-chloro-3-pyridyl)-5-(chloromethyl)-1H-1,2,4-triazole-3-carboxylic acid melts at 203°–205° with decomposition.

(c) A mixture of 50.00 g (0.183 mol) of the triazolecarboxylic acid prepared according to (b), 59.60 g (0.642 mol) of aniline and 0.05 g of potassium iodide in 1000 ml of ethanol is boiled under reflux for 24 hours. The reaction mixture is then concentrated to dryness by evaporation in vacuo and the residue is dissolved in 200 ml of ether and 500 ml of 1N sodium hydroxide solution. The alkaline aqueous phase is separated off, washed three times using 150 ml of ether each time and then rendered acidic to Congo red by the addition of concentrated hydrochloric acid. 150 ml of methylene chloride are added and the whole is stirred for one hour at 0° and the carboxylic acid that is formed is filtered off. After washing with water and methylene chloride, the product is dried in vacuo over calcium chloride. The resulting 5-phenyl-4,5-dihydropyrido[2,3-b][1,2,4]triazolo[1,5-a]pyrazine-2-carboxylic acid melts at 208°–213° with decomposition.

A further quantity of the same carboxylic acid is obtained by concentrating the methylene chloride phases of the mother liquor by evaporation.

(d) A suspension of 49.20 g (0.168 mol) of the carboxylic acid prepared according to (d) in 490 ml of methanol and 100 ml of 6N methanolic hydrochloric acid solution is boiled under reflux for 16 hours, a clear yellow solution being produced. The solution is then concentrated by evaporation in vacuo and the residue is dissolved in methylene chloride and ice-cold 1N potassium bicarbonate solution. The separated organic phase is washed once with cold 1N potassium bicarbonate solution and once with saturated sodium chloride solution, dried over sodium sulphate and concentrated by evaporation in vacuo. After recrystallisation of the residue from methylene chloride/isopropanol, 5-phenyl-4,5-dihydropyrido[2,3-e][1,2,4]triazolo[1,5-a]pyrazine-2-carboxylic acid methyl ester having a melting point of 198°–201° is obtained.

(e) While stirring, 23.6 g (0.625 mol) of sodium borohydride, divided into three portions, are added at room temperature to a suspension of 38.50 g (0.125 mol) of the ester prepared according to (e) in 1250 ml of methanol and 1250 mol of tetrahydrofuran. The reaction mixture foams vigorously and its temperature rises to from 33° to 35°, and that temperature is maintained by cooling gently. The mixture is then stirred for 90 minutes at room temperature and, after the addition of 1250 ml of ice-water, for a further 2 hours at 0°–5°. The precipitated product is filtered with suction and washed with water to pH 6 and ether. After drying over calcium chloride in vacuo, the resulting 5-phenyl-4,5-dihydropyrido[2,3-e][1,2,4]triazolo[1,5-a]pyrazine-2-methanol melts at 233°–237°.

EXAMPLE 7

After the addition of 88 ml (0.934 mol) of 33% ethanolic methylamine solution and 20 ml of ethanol, the crude methanesulphonic acid ester prepared according to Example 6 from 10.00 g (0.036 mol) of 5-phenyl-4,5-dihydropyrido[2,3-e][1,2,4]triazolo[1,5-a]pyriazine-2-methanol and 6.15 g (0.054 mol) of methanesulphonic acid chloride is stirred overnight at room temperature. The reaction mixture is then concentrated by evaporation in vacuo and the solid residue is dissolved in ethyl acetate and 1N potassium bicarbonate solution. The aqueous phase is separated off and extracted once more with ethyl acetate. The combined extracts are washed twice with water and once with saturated sodium chloride solution, dried over sodium sulphate and concentrated by evaporation in vacuo. The residue is dissolved in 200 ml of ethanol, and a saturated ethanolic fumaric acid solution is added until a sample to which water has been added has a pH value of 4. After 5 hours, the crystals that have precipitated are filtered off and recrystallised twice from ethanol. After drying, the resulting 2-[(methylamino)-methyl]-5-phenyl-4,5-dihydropyrido[2,3-e][1,2,4]triazolo[1,5-a]pyrazine furmarate (1:1) melts at 180°–183° with decomposition.

In analogous manner, using as starting material 5.00 g (0.018 mol) of 5-phenyl-4,5-dihydropyrido[2,3-e][1,2,4]triazolo[1,5-a]pyrazine-2-methanol there is obtained via the crude methanesulphonic acid ester thereof using 12.70 g (0.179 mol) of pyrrolidine, 2-[(1-pyrrolidinyl)-methyl]-5-phenyl-4,5-dihydropyrido[2,3-e][1,2,4]triazlo[1,5-a]pyrazine having a melting point of 110°–113° after recrystallisation from methylene chloride/isopropanol.

EXAMPLE 8

In a manner analogous to that described in Example 6:

using as starting material 12.20 g (0.039 mol) of 5-(2-chlorophenyl)-4,5-dihydropyrido[2,3-e][1,2,4]triazolo[1,5-a]pyrazine-2-methanol there is obtained via the crude methanesulphonic acid ester thereof using 53 ml (0.390 mol) of 33% ethanolic dimethylamine solution, 2-[(dimethylamino)-methyl]-5-(2-chlorophenyl)-4,5-dihydropyrido[2,3-e][1,2,4]triazolo[1,5-a]pyrazine of which the hydrochloride, prepared in ethyl acetate, melts at 224°–228°, with decomposition, after recrystallisation from isopropanol;

using as starting material 3.46 g (0.011 mol) of 5-(3-chlorophenyl)-4,5-dihydropyrido[2,3-e][1,2,4]triazolo[1,5-a]pyrazine-2-methanol there is obtained via the methanesulphonic acid ester thereof using 11 ml (0.08 mol) of 33% ethanolic dimethylamine solution, 2-[(dimethylamino)-methyl]-5-(3-chlorophenyl)-4,5-dihydropyrido[2,3-e][1,2,4]triazolo[1,5-a]pyrazine having a melting point of 97°–100° after crystallisation from methylene chloride/isopropanol;

using as starting material 6.85 g (0.022 mol) of 5-(4-chlorophenyl)-4,5-dihydropyrido[2,3-e][1,2,4]triazolo[1,5-a]pyriazine-2-methanol there is obtained via the methanesulphonic acid ester thereof using 39 ml (0.218 mol) of 33% ethanolic dimethylamine solution, 2-[(dimethylamino)-methyl]-5-(4-chlorophenyl)-4,5-dihydropyrido[2,3-e][1,2,4]triazolo[1,5-a]pyrazine having a melting point of 185°–188° after crystallisation from methylene chloride/isopropanol;

using as starting material 6.30 g (0.020 mol) of 5-(4-methoxyphenyl)-4,5-dihydropyrido[2,3-e][1,2,4]triazolo[1,5-a]pyrazine-2-methanol there is obtained via the crude methanesulphonic acid ester thereof using 21 ml (0.12 mol) of 33% ethanolic dimethylamine solution, 2-[(dimethylamino)-methyl]-5-(4-methoxyphenyl)-4,5-dihydropyrido[2,3-e][1,2,4]triazolo[1,5-a]pyrazine of which the hydrochloride, prepared in ethyl acetate, melts at 215°–222°, with decomposition, after recrystallisation from isopropanol, and using as starting material 20.20 g (0.071 mol) of 5-cyclohexyl-4,5-dihydropyrido[2,3-e][1,2,4]triazolo[1,5-a]pyrazine-2-methanol there is obtained via the crude methanesulphonic acid methyl ester thereof using 97 ml (0.71 mol) of 33% ethanolic dimethylamine solution, 2-[(dimethylamino)-methyl]-5-cyclohexyl-4,5-dihydropyrido[2,3-e][1,2,4]triazolo[1,5-a]pyrazine of which the hydrochloride, prepared in ethyl acetate, melts at 278°–281°, with decomposition, after recrystallisation from methylene chloride/isopropanol.

The starting materials required are prepared as follows:

(a) In a manner analogous to that described in Example (6c) and (6d):

using 31.40 g (0.115 mol) of 1-(2-chloro-3-pyridyl)-5-(chloromethyl)-1H-1,2,4-triazole-3-carboxylic acid and 206.00 g (1.61 mol) of 2-chloroaniline there is obtained 5-(2-chlorophenyl)-4,5-dihydropyrido[2,3-e][1,2,4]triazolo[1,5-a]pyrazine-2-carboxylic acid and the methyl ester thereof which, after recrystallisation from methylene chloride/isopropanol, melts at 155°–163°;

using 7.36 g (0.027 mol) of 1-(2-chloro-3-pyridyl)-5-(chloromethyl)-1H-1,2,4-triazole-3-carboxylic acid and 48.10 g (0.378 mol) of 3-chloroaniline there is obtained 5-(3-chlorophenyl)-4,5-dihydropyrido[2,3-e][1,2,4]triazolo[1,5-a]pyrazine-3-carboxylic acid and the methyl ester thereof which, after recrystallisation from methylene chloride/isopropanol, melts at 213°–216°;

using 8.91 g (0.033 mol) of 1-(2-chloro-3-pyridyl)-5-(chloromethyl)-1H-1,2,4-triazole-3-carboxylic acid and 20.90 g (0.164 mol) of p-chloroaniline there is obtained 5-(4-chlorophenyl)-4,5-dihydropyrido[2,3-e][1,2,4]triazolo[1,5-a]pyrazine-2-carboxylic acid and the methyl ester thereof which, after recrystallisation from methylene chloride/ethyl acetate, melts at 234°–237° with decomposition;

using 10.00 g (0.037 mol) of 1-(2-chloro-3-pyridyl)-5-(chloromethyl)-1H-1,2,4-triazole-3-carboxylic acid and 15.80 g (0.128 mol) of 4-methoxyaniline there is obtained 5-(4-methoxyphenyl)-4,5-dihydropyrido[2,3-e][1,2,4]triazolo[1,5-a]pyrazine-2-carboxylic acid and the methyl ester thereof which, after recrystallisation from methylene chloride/isopropanol, melts at 190°–196°;

using 21.80 g (0.080 mol) of 1-(2-chloro-3-pyridyl)-5-(chloromethyl)-1H-1,2,4-triazole-3-carboxylic acid and 35.70 g (0.360 mol) of cyclohexylamine there is obtained 5-cyclohexyl-4,5-dihydropyrido[2,3-e][1,2,4]triazolo[1,5-a]pyrazine-2-carboxylic acid and the methyl ester thereof which, after recrystallisation from methylene chloride/isopropanol, melts at 170°–176°.

(b) In a manner analogous to that described in Example (6e):

using 15.00 g (0.044 mol) of 5-(2-chlorophenyl)-4,5-dihydropyrido[2,3-e][1,2,4]triazolo[1,5-a]pyrazine-2-carboxylic acid methyl ester and 8.28 g (0.219 mol) of sodium borohydride there is obtained 5-(2-chlorophenyl)-4,5-dihydropyrido[2,3-e][1,2,4]triazolo[1,5-a]pyrazine-2-methanol having a melting point of 193°–196°;

using 3.80 g (0.011 mol) of 5-(3-chlorophenyl)-4,5-dihydropyrido[2,3-e][1,2,4]triazolo[1,5-a]pyrazine-2-carboxylic acid methyl ester and 4.20 g (0.112 mol) of sodium borohydride there is obtained 5-(3-chlorophenyl)-4,5-dihydropyrido[2,3-e][1,2,4]triazolo[1,5-a]pyrazine-2-methanol having a melting point of 204°–206°;

using 7.90 g (0.023 mol) of 5-(4-chlorophenyl)-4,5-dihydropyrido[2,3-e][1,2,4]triazolo[1,5-a]pyrazine-2-carboxylic acid methyl ester and 4.37 g (0.116 mol) of sodium borohydride there is obtained 5-(4-chlorophenyl)-4,5-dihydropyrido[2,3-e][1,2,4]triazolo[1,5-a]pyrazine-2-methanol having a melting point of 240°–245° with decomposition;

using 8.10 g (0.024 mol) of 5-(4-methoxyphenol)-4,5-dihydropyrido[2,3-e][1,2,4]triazolo[1,5-a]pyrazine-2-carboxylic acid methyl ester and 4.50 g (0.120 mol) of sodium borohydride there is obtained 5-(4-methoxyphenyl)-4,5-dihydropyrido[2,3-e][1,2,4]triazolo[1,5-a]pyrazine-2-methanol having a melting point of 226°–230°, and using 29.80 g (0.095 mol) of 5-cyclohexyl-4,5-dihydropyrido[2,3-e][1,2,4]triazolo[1,5-a]pyrazine-2-carboxylic acid methyl ester and 18.00 g (0.476 mol) of sodium borohydride there is obtained, after concentration of the reaction mixture by evaporation and extractive working up with methylene chloride, 5-cyclohexyl-4,5-dihydropyrido[2,3-e][1,2,4]triazolo[1,5-a]pyrazine-2-methanol which, after recrystallisation from methylene chloride/isopropanol, melts at 190°–194°.

EXAMPLE 9

At 0° under nitrogen, 4.70 g (0.041 mol) of methanesulphonic acid chloride are added dropwise over a period of 5 minutes to a solution of 8.00 g (0.027 mol) of 4-methyl-5-phenyl-4,5-dihydro-[1,2,4]triazolo[1,5-a]quinoxaline-2-methanol in 270 ml of absolute methylene chloride and 5.50 g (0.055 mol) of triethylamine. After stirring for one hour at from 0° to 4°, the clear reaction mixture is poured onto a mixture of ice and water, the organic phase is separated off and the aqueous phase is extracted once more with methylene chloride. The extracts are washed twice with ice-cold water and once with saturated sodium chloride solution, dried over sodium sulphate and concentrated to dryness by evaporation in vacuo.

The methanesulphonic acid ester of 4-methyl-5-phenyl-4,5-dihydro-[1,2,4]triazolo[1,5-a]quinoxaline-2-methanol, which is obtained as a residue of honey-like consistency, is reacted, without further purification, by adding a cold mixture of 37.5 ml (0.274 mol) of 33% ethanolic dimethylamine solution and 37.5 ml of ethanol and leaving the reaction mixture to stand in a closed container for 1 hour. The reaction mixture is then concentrated by evaporation in vacuo and the residue is dissolved in ethyl acetate and 1N potassium bicarbonate solution. The aqueous phase is separated off and extracted once more with ethyl acetate. The combined organic extracts are washed three times with water and once with saturated sodium chloride solution and dried over sodium sulphate. After filtering off the drying agent, ethereal hydrogen chloride solution is added dropwise, while stirring well, to the filtrate until a pH value of 3 has been reached. After leaving to stand at room temperature for 5 hours, the crude hydrochloride that has formed is filtered off and washed with ethyl acetate. It is then dissolved in 50 ml of methylene chloride and 100 ml of ethyl acetate. After evaporating off the methylene chloride in vacuo at 40°, the desired hydrochloride crystallises out again. The mixture is left to stand in a refrigerator for 2 hours and then the crystals are filtered off and washed with ethyl acetate. After drying under a high vacuum at 120°, the resulting 2-[(dimethylamino)-methyl]-4-methyl-5-phenyl-4,5-dihydro[1,2,4]triazolo[1,5-a]quinoxaline hydrochloride melts at 195°–198°.

The 4-methyl-5-phenyl-4,5-dihydro-[1,2,4]triazolo[1,5-a]quinoxaline-2-methanol required as starting material is prepared as follows:

(a) 30.0 ml (0.30 mol) of 2-chloropropionic acid chloride are added dropwise over a period of one hour to a suspension of 50.0 g (0.272 mol) of aminomalonic acid dimethyl ester hydrochloride in 250 ml of absolute methylene chloride. After boiling under reflux for 4 hours, the evolution of hydrogen chloride has ceased. The suspension is cooled to room temperature, 100 ml of ice-cold water are added and the organic phase is separated off and washed three times with water and once with saturated sodium chloride solution. After concentration by evaporation in vacuo, the residue is dissolved in 100 ml of methylene chloride; 400 ml of hexane are slowly added and the mixture is left to stand at room temperature for 2 hours. The crystals that have formed are then filtered off and washed with methylene chloride/hexane (1:4). After drying in vacuo, the resulting (2-chloropropionamido)-malonic acid dimethyl ester melts at 100°–102°.

(b) A solution of 26.20 g (0.102 mol) of the (2-aminophenyl)-phenylcarbamic acid ethyl ester prepared according to Example (1b) in 246 ml of glacial acetic acid and 62 ml of concentrated hydrochloric acid is diazotised at 0°–5° over a period of 20 minutes with 20.4 ml (0.102 mol) of a 5-molar sodium nitrite solution. 60 g of ice are added to the resulting diazonium salt solution, and then 24.23 g (0.102 mol) of (2-chloropropionamido)-malonic acid dimethyl ester in 243 ml of acetone are then quickly added dropwise. Then, at 0°–5°, 500 ml of a saturated potassium carbonate solution are added over a period of 30 minutes, the pH value finally being 6. After stirring for a further one hour at 0°–5, 300 ml of ethyl acetate are added, the organic phase is separated off and the aqueous phase extracted once more with ethyl acetate. The combined organic extracts are washed four times with water and twice with saturated sodium chloride solution, dried over sodium sulphate and concentrated by evaporation in vacuo, yielding the orange-colored [2-(N-ethoxycarbonylphenylamino)-phenylazo]-(2-chloropropionamido)-malonic acid dimethyl ester which is of honey-like consistency. It can be used in the next stage without further purification.

(c) While stirring well, a solution of 53.0 g (approximately 0.102 mol) of the azo compound prepared according to (b) in 530 ml of methanol is added over a period of 3 minutes to 316 ml (0.316 mol) of 1N sodium hydroxide solution pre-cooled to 0° C. The mixture is stirred at room temperature for a further 90 minutes and then glacial acetic acid is added dropwise until the pH value has reached 5. 2N hydrochloric acid is added to the clear solution until it is acidic to Congo red. 350 ml of water are then added dropwise to the reaction mixture over a period of 3 hours, crystallisation gradually taking place. After stirring at 0° for 6 hours, the crystals that have formed are filtered off and washed with generous amounts of water. After drying over calcium chloride in vacuo, the resulting 1-[2-(N-ethoxycarbonylphenylamino)-phenyl]-5-(1-chloroethyl)-1H-[1H-[1,2,4]triazole-3-carboxylic acid melts at 153°–156°.

(d) A suspension of 37.90 g (0.091 mol) of the carboxylic acid prepared according to (c) in 210 ml of 48% hydrobromic acid is stirred for 12 hours under nitrogen at a bath temperature of 105°, a clear green solution being produced. The reaction mixture is then cooled to room temperature and, under nitrogen, 530 ml of water are added over a period of 90 minutes. After cooling to 0° for 3 hours, the carboxylic acid is filtered with suction, washed with a total of 600 ml of water to pH 4 and dried over calcium chloride in a vacuum dessicator. The resulting 4-methyl-5-phenyl-4,5-dihydro-[1,2,4]triazolo[1,5-a]quinoxaline-2-carboxylic acid sinters at 176° and melts from 181° with decomposition.

(e) A suspension of 26.70 g (0.087 mol) of the carboxylic acid prepared according (d) in 535 ml of methanol and 106 ml of 6N methanolic hydrochloric acid solution is stirred under nitrogen for 16 hours at boiling temperature under reflux, a clear light-yellow solution quickly being produced. The reaction mixture is then concentrated to dryness by evaporation in vacuo. The residue is dissolved in methylene chloride and ice-water, the organic phase is separated off and the aqueous phase is extracted once more with methylene chloride. The combined organic extracts are washed twice with ice-cold 1N potassium bicarbonate solution and twice with saturated sodium chloride solution, dried over sodium sulphate and concentrated by evaporation in vacuo. To the residue, which has a honey-like consistency, there are added 60 ml of ether and, thereafter, 60 ml of hexane. After 4 hours, the crystals that have formed are filtered off and washed with ether/hexane (1:1). After drying in vacuo, the resulting 4-methyl-5-phenyl-4,5-dihydro-[1,2,4]triazolo[1,5-a]quinoxaline-2-carboxylic acid methyl ester sinters at 134° and melts at 139°–141°.

(f) At room temperature under nitrogen, a total of 5.48 g (0.145 mol) of sodium borohydride, divided into three portions, is added, while stirring, over a period of 10 minutes to a solution of 16.60 g (0.052 mol) of the ester prepared according to (e) in 166 ml of methanol and 166 ml of tetrahydrofuran. The reaction mixture foams vigorously and its temperature rises to 29°. The mixture is stirred at room temperature for 3 hours and, after the addition of 335 ml of a mixture of ice and water, for a further 2 hours at 0°. The alcohol that is precipitated is filtered with suction and washed with water to pH 6. After drying over calcium chloride in a vacuum desiccator, the resulting 4-methyl-5-phenyl-4,5-dihydro-[1,2,4]triazolo[1,5-a]quinoxaline-3-methanol sinters at 150° and melts at 157°–160°.

EXAMPLE 10

At 0°–2° under nitrogen, 55.40 ml (0.066 mol) of a 1.2 molar solution of diisobutylaluminium hydride in toluene are added dropwise over a period of 20 minutes to a solution of 7.70 g (0.022 mol) of N,N,4,4-tetramethyl-5-phenyl-4,5-dihydro-[1,2,4]triazolo[1,5-a]quinoxaline-2-carboxamide in 1100 ml of absolute toluene. The reaction mixture is stirred for a further 1 hour at 5°, then 15 ml of isopropanol are added dropwise thereto, followed by 160 ml of ice-cold water and as much concentrated sodium hydroxide solution as is necessary for the pH value to reach 11. The organic phase is separated off and the aqueous phase is extracted once more with toluene. The combined organic extracts are washed twice with 2N sodium hydroxide solution, twice with water and once with saturated sodium chloride solution, dried over sodium sulphate and concentrated by evaporation in vacuo. The residue, which is of honey-like consistency, is dissolved in ethyl acetate and the solution is chromatographed over a column of 180 g of silica gel, first with 2 l of ethyl acetate and then with 3 l of methylene chloride/methanol (95:5). The fractions that contain the desired product are concentrated by evaporation in vacuo and dissolved in ethyl acetate and, while stirring, ethereal hydrogen chloride solution is added until a pH value of 4 has been reached. After stirring for one hour in an ice bath, the pure hydrochloride that has formed is filtered off and washed with ethyl acetate. After drying under a high vacuum at 80° over potassium hydroxide, the resulting 4,4-dimethyl-2-[(dimethylamino)-methyl]-5-phenyl-4,5-dihydro-[1,2,4]triazolo[1,5-a]quinoxaline hydrochloride melts at 206°–207°.

The N,N,4,4-tetramethyl-5-phenyl-4,5-dihydro-[1,2,4]triazolo[1,5-a]quinoxaline-2-carboxamide required as starting material is prepared as follows:

(a) A solution of 18.0 g (0.056 mol) of the 4-methyl-5-phenyl-4,5-dihydro-[1,2,4]triazolo[1,5a]quinoxaline-2-carboxylic acid methyl ester prepared according to Example (9e) in 900 ml of methanol and 154 ml (1.12 mol) of 33% ethanolic dimethylamine solution is stirred in a closed container for 24 hours. The reaction mixture is then concentrated by evaporation in vacuo and the residue is dissolved in methylene chloride and a mixture of ice and water. The organic phase is washed twice with cold 5% potassium bicarbonate solution and once with saturated sodium chloride solution, dried over sodium sulphate and concentrated by evaporation in vacuo. After recrystallization of the residue from 100 ml of isopropanol and drying over calcium chloride in a vacuum desiccator the resulting N,N,4-trimethyl-5-phenyl-4,5-dihydro-[1,2,4]triazolo[1,5-a]quinoxaline-2-carboxamide melts at 150°–152°.

(b) Under nitrogen, 16 ml (0.026 mol) of a 1.6 molar solution of butyllithium in hexane are added dropwise, using a syringe, over a period of 15 minutes to a solution, cooled to −70°, of 3.60 ml (0.026 mol) of diisopropylamine in 78 ml of absolute tetrahydrofuran. The clear yellowish reaction solution is stirred at −10° for 5 minutes. After again cooling to −70°, there is added dropwise, over a period of 30 minutes, a solution of 7.80 g (0.023 mol) of the carboxylic acid amide prepared according to Example 10(b) in 4.5 ml of hexamethylphosphoric acid triamide and 31 ml of absolute tetrahydrofuran. The deep brown-red solution is stirred for 15 minutes at −70° and, after the addition of 3.20 ml (0.051 mol) of methyl iodide, for a further 90 minutes at −70°. The temperature of the reaction solution is allowed to rise to 0° and the solution is then poured onto a mixture of ice and water and extracted twice with ethyl acetate. The organic extracts are washed twice with ice-cold 2N hydrochloric acid, twice with 1N potassium bicarbonate solution and once with saturated sodium chloride solution, dried over sodium sulphate and concentrated to dryness by evaporation in vacuo. The residue, which is of honey-like consistency and slowly begins to crystallise, is dissolved in ethyl acetate and the solution is chromatographed over a column of 200 g of silica gel using ethyl acetate as eluant. The fractions, which contain the desired product, are combined and recrystallised from isopropanol. After drying over calcium chloride in a vacuum desiccator, the resulting N,N,4,4-tetramethyl-5-phenyl-4,5-dihydro-[1,2,4]triazolo[1,5-a]quinoxaline-2-carboxamide melts at 147°–149°.

EXAMPLE 11

Tablets containing 100 mg of 2-[(dimethylamino)-methyl]-5-phenyl-4,5-dihydro-[1,2,4]triazolo[1,5-a]quinoxaline hydrochloride as active ingredient can be manufactured, for example, having the following composition:

| Composition | per tablet |
| --- | --- |
| active ingredient | 100 mg |
| lactose | 50 mg |
| wheat starch | 73 mg |
| colloidal silica | 13 mg |
| talc | 12 mg |
| magnesium stearate | 2 mg |
| | 250 mg |

Manufacture

The active ingredient is mixed with the lactose, a portion of the wheat starch and with the colloidal silica and the mixture is forced through a sieve. A further portion of the wheat starch is made into a paste with 5 times the quantity of water on a water bath and the pulverulent mixture is kneaded with this paste until a slightly plastic mass has been produced. The mass is forced through a sieve is approximately 3 mm mesh width and dried, and the dry granulate is again forced through a sieve. Then the remainder of the wheat starch, the talc and magnesium stearate are mixed in. The resulting mixture is pressed to form 250 mg tablets having (a) breaking notch(es).

EXAMPLE 12

In a manner analogous to that described in Example 11 it is possible to manufacture tablets each containing 50 mg of the active ingredient, using 50 mg of 2-[(dimethylamino)-methyl]-5-phenyl-4,5-dihydro-[1,2,4]-triazolo[1,5-a]quinoxaline and 100 mg of lactose per tablet.

EXAMPLE 13

For the manufacture of 1000 capsules each containing 100 mg of active ingredient, 100 g of 2-[(dimethylamino)-methyl]-5-phenyl-4,5-dihydro-[1,2,4]triazolo[1,5-a]quinoxaline hydrochloride are mixed with 173.0 g of lactose, the mixture is moistened uniformly with an aqueous solution of 2.0 g of gelatine and granulated through a suitable sieve (for example sieve III according to Ph. Helv. V.). The granulate is mixed with 10.0 g of dried maize starch and 15.0 g of talc, and 1000 size 1 hard gelatine capsules are filled with equal quantities of this mixture.

Instead of 2-[(dimethylamino)-methyl]-5-phenyl-4,5-dihydro-[1,2,4]triazolo[1,5-a]quinoxaline hydrochloride it is also possible to use the above Examples 11, 12 and 13 a pharmaceutically acceptable acid solution salt of a different compound of the general formula I.

What is claimed is:
1. A polycyclic polyazaheterocycle of the formula I

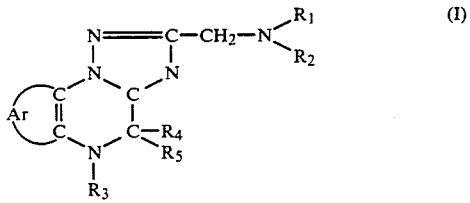

in which
R$_1$ and R$_2$ each represents, independently of one another, hydrogen, lower alkyl or hydroxy-lower alkyl, or together represent lower alkylene or ethyleneoxyethylene, ethyleneaza-ethylene or N-lower alkyl- or N-(2-hydroxy-lower alkyl)-ethyleneazaethylene;
R$_3$ represents a lower aliphatic hydrocarbon radical, a saturated lower cycloaliphatic hydrocarbon radical, or phenyl which is unsubstituted or substituted by halogen having an atomic number up to 35, lower alkyl, lower alkoxy, lower alkylthio, trifluoromethyl, cyano or nitro;
R$_4$ and R$_5$ represent hydrogen or lower alkyl; and Ar represents a benzo or pyrido(2,3-e) radical that are unsubstituted or substituted by halogen having an atomic number up to 35, lower alkyl, lower alkoxy, lower alkylthio, trifluoromethyl, cyano or nitro;
and the pharmaceutically acceptable acid addition salts thereof.

2. A method for treating conditions of depression or anxiety in a mammal comprising administering to said mammal a therapeutically effective amount of a compound according to claim 1 or of a pharmaceutically acceptable acid addition salt thereof.

3. A compound according to claim 1 having formula I in which R$_1$ represents lower alkyl and R$_2$ represents hydrogen or lower alkyl, or R$_1$ and R$_2$ together represent lower alkylene, R$_3$ represents phenyl that is unsubstituted or substituted by halogen having an atomic number of up to 35, or represents lower cycloalkyl, and Ar represents a benzo or pyrido[2,3-e] radical that is unsubstituted or substituted by halogen having an atomic number of up to 35, and the pharmaceutically acceptable acid addition salts thereof.

4. A compound according to claim 1 having formula I in which R$_1$ represents lower alkyl and R$_2$ represents hydrogen or lower alkyl, or R$_1$ and R$_2$ together represent lower alkylene, R$_3$ represents phenyl that is unsubstituted or substituted by halogen having an atomic number of up to 35, and Ar represents a benzo radical that is unsubstituted or substituted by halogen having an atomic number of up to 35, or represents the pyrido[2,3-e] radical, and R$_5$ represents hydrogen or methyl, and the pharmaceutically acceptable acid addition salts thereof.

5. A compound according to claim 1 having formula I in which R$_1$ represents methyl and R$_2$ represents hydrogen, or R$_1$ and R$_2$ together represent tetramethylene, R$_3$ represents phenyl that is unsubstituted or substituted by chlorine, and Ar represents a benzo radical that is unsubstituted or substituted by chlorine, or represents the pyrido[2,3-e] radical, R$_4$ represents hydrogen or methyl, and R$_5$ represents hydrogen or methyl, and the pharmaceutically acceptable acid addition salts thereof.

6. A compound according to claim 1 having formula I in which R$_1$ represents methyl, R$_2$ represents hydrogen or methyl, R$_3$ represents phenyl, R$_4$ represents hydrogen or methyl, R$_5$ represents hydrogen or methyl, and Ar represents the benzo or pyrido[2,3-e] radical, and the pharmaceutically acceptable acid addition salts thereof.

7. A compound according to claim 1 which is 2-[(dimethylamino)-methyl]-5-phenyl-4,5-dihydro-[1,2,4]triazolo[1,5-a]quinoxaline and its pharmaceutically acceptable acid addition salts.

8. A compound according to claim 1 which is 2-[(methylamino)-methyl]-5-phenyl-4,5-dihydro-[1,2,4]triazolo[1,5-a]quinoxaline and acid addition salts.

9. A compound according to claim 1 which is 2-[(diethylamino)-methyl]-5-phenyl-4,5-dihydro-[1,2,4]triazolo[1,5-a]quinoxaline and its pharmaceutically acceptable acid addition salts.

10. A compound according to claim 1 which is 2-[(piperidino)-methyl]-5-phenyl-4,5-dihydro-[1,2,4]-triazolo[1,5-a]quinoxaline and acid addition salts.

11. A compound according to claim 1 which is 2-[(dimethylamino)-methyl]-5-(4-chlorophenyl)-4,5-dihydro-[1,2,4]triazolo[1,5-a]quinoxaline and its pharmaceutically acceptable acid addition salts.

12. A compound according to claim 1 which is 2-[(dimethylamino)-methyl]-5-[3-(trifluoromethyl)-phenyl]-4,5-dihydro-[1,2,4]triazolo[1,5-a]quinoxaline and its pharmaceutically acceptable acid addition salts.

13. A compound according to claim 1 which is 2-[(dimethylamino)-methyl]-5-(2,3-dimethylphenyl)-4,5- dihydro-[1,2,4]triazol[1,5-a]quinoxaline and its pharmaceutically acceptable acid addition salts.

14. A compound according to claim 1 which is 7-chloro-2-[(dimethylamino)-methyl]-5-phenyl-4,5-dihydro-[1,2,4]triazolo[1,5-a]quinoxaline and its pharmaceutically acceptable acid addition salts.

15. A compound according to claim 1 which is 8-chloro-2-[(dimethylamino)-methyl]-5-(2,4-dichlorophenyl)-4,5-dihydro-[1,2,4]triazolo[1,5-a]quinoxaline and its pharmaceutically acceptable acid addition salts.

16. A compound according to claim 1 which is 2-[(dimethylamino)-methyl]-4-methyl-5-phenyl-4,5-dihydro-[1,2,4]triazolo[1,5-a]quinoxaline and its pharmaceutically acceptable acid addition salts.

17. A compound according to claim 1 which is 4,4-dimethyl-2-[(dimethylamino)-methyl]-5-phenyl-4,5-dihydro-[1,2,4]triazolo[1,5-a]quinoxaline and its pharmaceutically acceptable acid addition salts.

18. A compound according to claim 1 which is 2-[(dimethylamino)-methyl]-5-phenyl-4,5-dihydropyrido[2,3-e][1,2,4]triazolo[1,5-a]pyrazine and its pharmaceutically acceptable acid addition salts.

19. A compound according to claim 1 which is 2-[(methylamino)-methyl]-5-phenyl-4,5-dihydropyrido[2,3-e][1,2,4]triazolo[1,5-a]pyrazine and its pharmaceutically acceptable acid addition salts.

20. A compound according to claim 1 which is 2-[(1-pyrrolidinyl)-methyl]-5-phenyl-4,5-dihydropyrido[2,3-e][1,2,4]triazolo[1,5-a]pyrazine and its pharmaceutically acceptable acid addition salts.

21. A pharmaceutical preparation having antidepressive and anxiolytic activity comprising a therapeutically effective amount of a compound according to claim 1, or of a pharmaceutically acceptable acid addition salt of such a compound, together with at least one pharmaceutical carrier.

22. A pharmaceutical preparation having antidepressive and anxiolytic activity comprising a therapeutically effective amount of a compound according to claim 3, or of a pharmaceutically acceptable acid addition salt of such a compound, together with at least one pharmaceutical carrier.

23. A pharmaceutical preparation having antidepressive and anxiolytic activity comprising a therapeutically effective amount of a compound according to claim 4, or of a pharmaceutically acceptable acid addition salt of such a compound, together with at least one pharmaceutical carrier.

24. A pharmaceutical preparation having antidepressive and anxiolytic activity comprising a therapeutically effective amount of 2-[(dimethylamino)-methyl]-5-phenyl-4,5-dihydro-[1,2,4]triazolo[1,5-a]quinoxaline or of a pharmaceutically acceptable acid addition salt thereof, together with at least one pharmaceutical carrier.

25. A method according to claim 2 comprising administering a therapeutically effective amount of 2-[(dimethylamino)-methyl]-5-phenyl-4,5-dihydro-[1,2,4]triazolo[1,5-a]quinoxaline or of a pharmaceutically acceptable acid addition salt thereof.

* * * * *